US011479752B2

(12) United States Patent
Ekser

(10) Patent No.: US 11,479,752 B2
(45) Date of Patent: Oct. 25, 2022

(54) SCAFFOLD-FREE 3D BIOPRINTING OF PORCINE CELLS

(71) Applicant: Indiana University Research and Technology Corporation, Indianapolis, IN (US)

(72) Inventor: Burcin Ekser, Indianapolis, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 466 days.

(21) Appl. No.: 16/162,921

(22) Filed: Oct. 17, 2018

(65) Prior Publication Data
US 2019/0119626 A1  Apr. 25, 2019

Related U.S. Application Data

(60) Provisional application No. 62/574,809, filed on Oct. 20, 2017.

(51) Int. Cl.
| | |
|---|---|
| *C12N 5/00* | (2006.01) |
| *B33Y 80/00* | (2015.01) |
| *C12N 5/071* | (2010.01) |
| *G01N 33/50* | (2006.01) |
| *B33Y 10/00* | (2015.01) |
| *B33Y 70/00* | (2020.01) |
| *A61L 27/38* | (2006.01) |

(52) U.S. Cl.
CPC ........ *C12N 5/0062* (2013.01); *A61L 27/3839* (2013.01); *B33Y 10/00* (2014.12); *B33Y 70/00* (2014.12); *B33Y 80/00* (2014.12); *C12N 5/0671* (2013.01); *C12N 5/0688* (2013.01); *G01N 33/5082* (2013.01); *G01N 33/5088* (2013.01); *A61L 2430/16* (2013.01); *A61L 2430/20* (2013.01); *A61L 2430/26* (2013.01); *C12N 2513/00* (2013.01); *C12N 2535/00* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis |
| 8,241,905 | B2 | 8/2012 | Forgacs |
| 8,852,932 | B2 | 10/2014 | Forgacs |
| 9,149,952 | B2 | 10/2015 | Murphy |
| 9,151,744 | B2 | 10/2015 | Pongracz et al. |
| 9,222,932 | B2 | 12/2015 | Shepherd |
| 9,481,868 | B2 | 11/2016 | Nguyen |
| 2002/0190663 | A1 | 12/2002 | Rasmussen |
| 2014/0093932 | A1 | 4/2014 | Murphy |
| 2014/0295548 | A1* | 10/2014 | Nyberg ............... A61M 1/3472 435/370 |
| 2017/0087766 | A1 | 3/2017 | Chung |

FOREIGN PATENT DOCUMENTS

| | | |
|---|---|---|
| WO | 2014066505 A1 | 5/2014 |
| WO | 2017090777 A1 | 6/2017 |

OTHER PUBLICATIONS

Fodor et al., Reproductive Biology and Endocrinology 2003, 1:102, pp. 1-6 (Year: 2003).*
Moldovan et al., Tissue Eng Part B Rev 2017; 23: 237-244 (Year: 2017).*
Norotte et al., Biomaterials 30 (2009) 5910-5917 (Year: 2009).*
O'Leary et al., Tissue Engineering: Part B, vol. 21, No. 4, 2015, pp. 323-344 (Year: 2015).*
Sommaggio et al.,(European Cells and Materials vol. 32, 2016 (pp. 24-39 (Year: 2016).*
Tseng et al., Tissue Eng Part C Methods, 2013; 19 (9): 665-675 (Year: 2013).*
Zeyland et al., J Appl Genetics (2013) 54: 293-303 (Year: 2013).*
MIH BRG (R01) PAR-16-242. Available from: https://grants.nih.gov/grants/guide/pa-files/PAR-16-242.html.
NIH EBRG (R21) PA-16-040. Available from: (https://grants.nih.gov/grants/guide/pa-files/PA-16-040.html).
Ong, C. S., et al. "Biomaterial-free three-dimensional bioprinting of cardiac tissue using human induced pluripotent stem cell derived cardiomyocytes." Scientific reports 7.1 (2017): 1-11.
Riccalton-Banks L, et al. Long-Term Culture of Functional Liver Tissue: Three-Dimensional Coculture of Primary Hepatocytes and Stellate Cells. Tissue Engineering. Jun. 2003;9(3):401-10.
Samy, K. P., et al. "The role of costimulation blockade in solid organ and islet xenotransplantation." Journal of immunology research 2017 (2017).
Sego TJ, et al. A heuristic computational model of basic cellular processes and oxygenation during spheroid-dependent biofabrication. Biofabrication. 2017;9(2):024104.
Skedros JG, et al. Analysis of the Effect of Osteon Diameter on the Potential Relationship of Osteocyte Lacuna Density and Osteon Wall Thickness. Anatomical record (Hoboken, NJ : 2007). 2011;294(9):1472-85.
Smith L. The Future is BRITE: A Technology Platform for Advancing Biofabrication. Personal communication in IUPUI—Johns Hopkins U Joint Symposium In Progress in Scaffold-Free Biofabrication. Indianapolis, IN Sep. 15, 2017.

(Continued)

*Primary Examiner* — Evelyn Y Pyla
(74) *Attorney, Agent, or Firm* — Quarles & Brady, LLP

(57) ABSTRACT

Provided herein are synthetic, three-dimensional (3D) bioprinted tissue constructs comprising porcine cells and methods of producing and using the same. The synthetic 3D bioprinted tissue constructs are fabricated by bioprinting spheroids comprising porcine cells, including genetically engineered cells, on a microneedle mold and fusing the spheroids to form an engineered tissue construct. Also provided are methods of using scaffold-free 3D bioprinted tissue constructs for applications related to drug screening and toxicity screening.

3 Claims, 26 Drawing Sheets
(24 of 26 Drawing Sheet(s) Filed in Color)

(56) References Cited

OTHER PUBLICATIONS

Smith, L. J., et al. "FABRICA: a bioreactor platform for printing, perfusing, observing, & stimulating 3D tissues." Scientific reports 8.1 (2018): 1-10.
Soldatow Vy, et al. In vitro models for liver toxicity testing. Toxicol Res. Jan. 1, 2013;2(1):23-39.
Souza GR, et al. Three-dimensional tissue culture based on magnetic cell levitation. Nat Nanotechnol 2010;5:291-296.
Stewart, R, et al. "Comparative RNA-seq analysis in the unsequenced axolotl: the oncogene burst highlights early gene expression in the blastema." PLoS Comput Biol 9.3 (2013): e1002936.
Tong WH, et al. Constrained spheroids for prolonged hepatocyte culture. Biomaterials 2016;80:106-120.
Tostoes RM, et al. Human liver cell spheroids in extended perfusion bioreactor culture for repeated-dose drug testing. Hepatology. 2012;55(4):1227-36.
Wong SF, et al. Concave microwell based size-conlrollable hepatosphere as a three-dimensional liver tissue model. Biomaterials. 2011;32(32):8087-96.
Abu-Absi SF, et al. Three-dimensional co-culture of hepatocytes and stellate cells. Cytotechnology. Apr. 8, 2004;45 (3):125-40.
American Association for the Study of Liver Diseases. Innovation Fund Webpage. Available from: https://www.aasld.org/membership/special-interest-groups/innovation-fund. Version dated Jan. 20, 2017.
Bonfiglio A, et al. Mathematical Modeling of the Circulation in the Liver Lobule. Journal of Biomechanical Engineering. 2010;132(11):111011-10. doi: 10.1115/1.4002563.
Burton AC. Relation of structure to function of the tissues of the wall of blood vessels. Physiol Rev. 1954;34(4):619-42. Epub Oct. 1, 1954. PubMed PMID: 13215088.
Carmeliet P, et al. Angiogenesis in cancer and other diseases. Nature. 2000;407(6801):249-57.
De L'Hortet A.C. et al. Liver Regenerative-Transplantation: Regrow and Reboot. Am J Transplant 2016; 16:1688-1696.
Cooper DK, et al. Pig liver xenotransplantation: a review of progress towards the clinic. Transplantation 2016; 100:2039-2047.
Cooper DK, et al. "The role of genetically engineered pigs in xenotransplantation research." The Journal of pathology 238.2 (2016): 288-299.
Dimmeler, S., et al. "Shear stress inhibits apoptosis of human endothelial cells." FEBS letters 399.1-2 (1996): 71-74.
Ekser B, et al. "Xenotransplantation: past, present, and future." Current opinion in organ transplantation 22.6 (2017):513.
Ekser B, et al. Clinical Xenotransplantation: the next medical revolution. Lancet 2012;379:672-683.
Ekser B, et al. Current status of pig liver xenotransplantation. Int J Surg 2015;23:240-246.
Ekser B, et al. Genetically-engineered pig-to-baboon liver xenotransplantation: histopathology ofxenograflsand native organs. PLos One 2012;7:e29720.
Ekser B, et al. Hepatic function after genetically engineered pig liver transplantation in baboons. Transplantation 2010;90:483-493.
Ekser B, et al. Impact of thrombocytopenia on survival of baboons with genetically modified pig liver transplants: clinical relevance. Am J Transplant 2010;10:273-285.
Ekser B, et al. Overcoming the barriers to xenotransplantation: prospects for the future. Expert Rev Clin Immunol 2010;6:219-230.
Ekser B, et al. Pig liver xenotransplantation as a bridge to allotransplantation: which patients might benefit? Transplantation 2009;88:1041-1049.
Ekser B, et al. Potential factors influencing the development of thrombocytopenia and consumptive coagulopathy after genetically modified pig liver xenotransplantation. Transpl Int 2012;25:882-896.
Ekser B, et al. The need for xenotransplantation asasouceoforgans and cells for clinical transplantation. Int J Surg 2015;23:199-204.
Estrada, Jose L., et al. "Evaluation of human and non-human primate antibody binding to pig cells lacking GGTA 1/CMAH/β4Gal NT 2 genes." Xenotransplantation 22.3 (2015): 194-202.
GAN L-m, et al. Distinct Regulation of Vascular Endothelial Growth Factor in Intact Human Conduit Vessels Exposed to Laminar Fluid Shear Stress and Pressure. Biochemical and Biophysical Research Communications. 2000;272(2):490-6.
Godoy P, et al. Recent advances in 2D and 3D in vitro systems using primary hepatocytes, alternative hepatocyte sources and non-parenchymal liver cells and their use in investigating mechanisms of hepatotoxicity, cell signaling and ADME. Arch Toxicol 2013;87:1315-1530.
Grimes DR, et al. A method for estimating the oxygen consumption rate in multicellular tumour spheroids. Journal of The Royal Society Interface. 2014;11(92).
Groll J, et al. Biofabrication: reappraising the definition of an evolving field. Biofabrication 2016;8:013001.
Groth DS, et al. Blood flow velocity measurements: a comparison of 25 clinical ultrasonographic units. J Ultrasound Med. 1995; 14(4): 273-7. Epub Apr. 1, 1995. PubMed PMID: 7602684.
Haisler WL, et al. Three-dimensional cell culturing by magnetic levitation. Nat Protoc 2013;8:1940-1949.
Horvath, L., et al. "Engineering an in vitro air-blood barrier by 3D bioprinting." Scientific reports 5.1 (2015): 1-8.
International Searching Authority. International Search Report and Written Opinion for application PCT/US2018/056250. dated Jan. 17, 2019. 18 pages.
Itoh M, et al. Scaffold-Free Tubular Tissues Created by a Bio-3D Printer Undergo Remodeling and Endothelialization when Implanted in Rat Aortae. PLoS One 2015;10:e0136681.
Wase H, et al. The role of platelets in coagulation dysfunction in xenotransplantation, and therapeutic options. Xenotransplantation 2014;21:201-220.
Jackson, B. 3D Systems Enters Bioprinting Agreement for Solid-Organs, Starting With the Lungs. 3dprintingindustry.com. Accessed online at https://3dprintingindustry.com/news/3d-systems-enters-bioprinting-agreement-solid-organs-starting-lungs-111720/. Published Apr. 26, 2017.
John Templeton Foundation. Science and the Big Questions webpage. Available from: https://www.templeton.org/funding-areas/science-big-questions. Version accessed on Jul. 9, 2017.
Jones Eav, et al. Measuring hemodynamic changes during mammalian development. American Journal of Physiology—Heart and Circulatory Physiology. 2004;287(4):H1561-H1569.
Jones Eav, et al. What Determines Blood Vessel Structure? Genetic Prespecification vs. Hemodynamics. Physiology. 2006;21(6):388-95.
Kang HW, et al. A 3D bioprinting system to produce human-scale tissue constructs with structural integrity. Nat Biotechnol 2016;34:312-319.
Kaul H, et al. A Multi-Paradigm Modeling Framework to Simulate Dynamic Reciprocity in a Bioreactor. PLoS ONE. 2013;8(3):e59671.
Kizawa H, et al. Scaffold-free 3D bio-printed human liver tissue stably maintains metabolic functions useful for drug discovery. Biochem Biophys Rep 2017; 10: 186-191.
Lee JH, et al. Potentiality of immobilized pig hepatocyte spheroids in bioartificial liver system. Transplant Proc 2012;44:1012-1014.
Li P., et al. Scaffold-free 3D-bioprinting (3DBP) of genetically-engineered pig cells. Xenotransplantation 2017; 24(5):56.
Li, P., et al. "Efficient generation of genetically distinct pigs in a single pregnancy using multiplexed single-guide RNA and carbohydrate selection." Xenotransplantation 22.1 (2015): 20-31.
Li, P., et al. "Identification of novel xenoreactive non-gal antigens: tetraspanin CD37 and CD81" Xenotransplantation. vol. 24. No. 5. 2017.
Maniatis et al., Molecular Cloning: A Laboratory Manual, Cold Spring Harbor, N.Y., pp. 280-281 (1982).
Messina A, et al. Self-assembly of tissue spheroids on polymeric membranes. J Tissue Eng Regen Med 2015. doi: 10.1002/term.2105.
Mironov V, et al. Organ printing: tissue spheroids as building blocks. Biomaterials 2009;30:2164-2174.
Moldovan Ni, et al. Principles of the Kenzan method for robotic cell spheroid-based three-dimensional bioprinting. Tissue Eng Part B Rev 2017; 23: 237-244.

(56) References Cited

OTHER PUBLICATIONS

Moldovan, L. et al. "iPSC-derived vascular cell spheroids as building blocks for scaffold-free biofabrication." Biotechnology Journal 12.12 (2017): 1700444.
Murata D, et al. A preliminary study of osteochondral regeneration using a scaffold-free three-dimensional construct of porcine adipose tissue-derived mesenchymal stem cells. J Orthop Surg Res 2015;10:35.
Murphy SV, et al. 3D bioprinting of tissues and organs. Nat Biotechnol 2014;32:773-785.
NASA Vascular Tissue Challenge webpage. Version accessed on May 11, 2017. Available from: https://neworgan.org/vtc-prize.php.
Nguyen, D. G., et al. "Bioprinted 3D primary liver tissues allow assessment of organ-level response to clinical drug induced toxicity in vitro." PloS one 11.7 (2016): e0158674.
Jana et al., Bioprinting a Cardiac Valve, Biotechnology Advances, 2015, 33:1503-1521.
European Patent Office, Extended European Search Report, Application No. 18869417.8, dated Jul. 1, 2021, 15 pages.

\* cited by examiner

FIGS. 3A-3D, CONTINUED
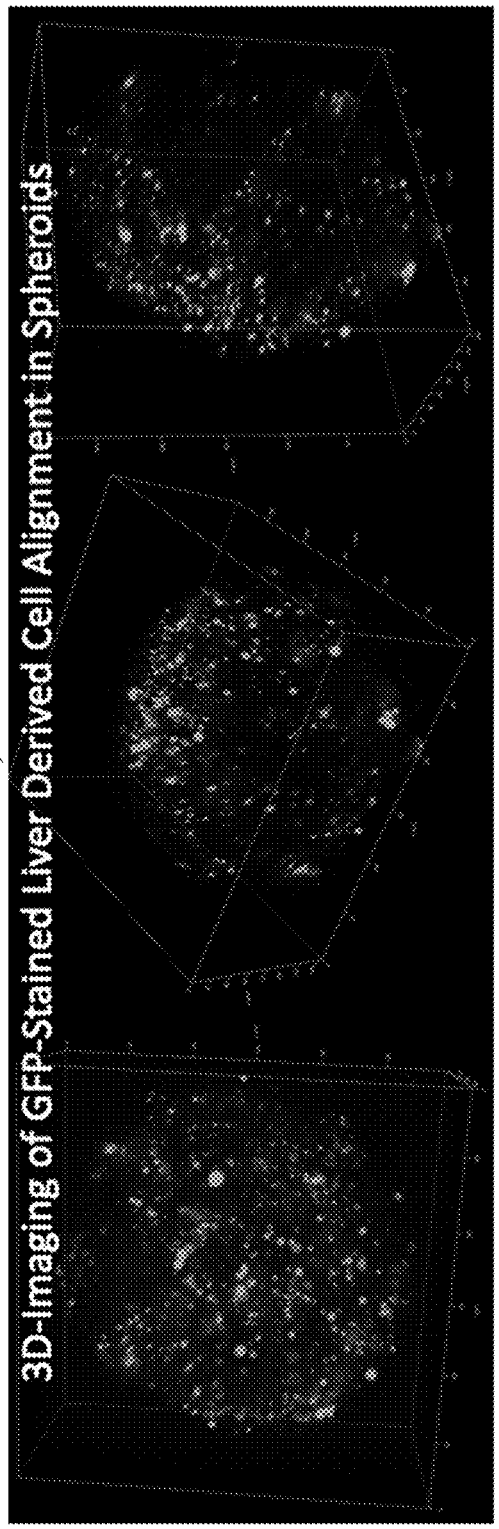
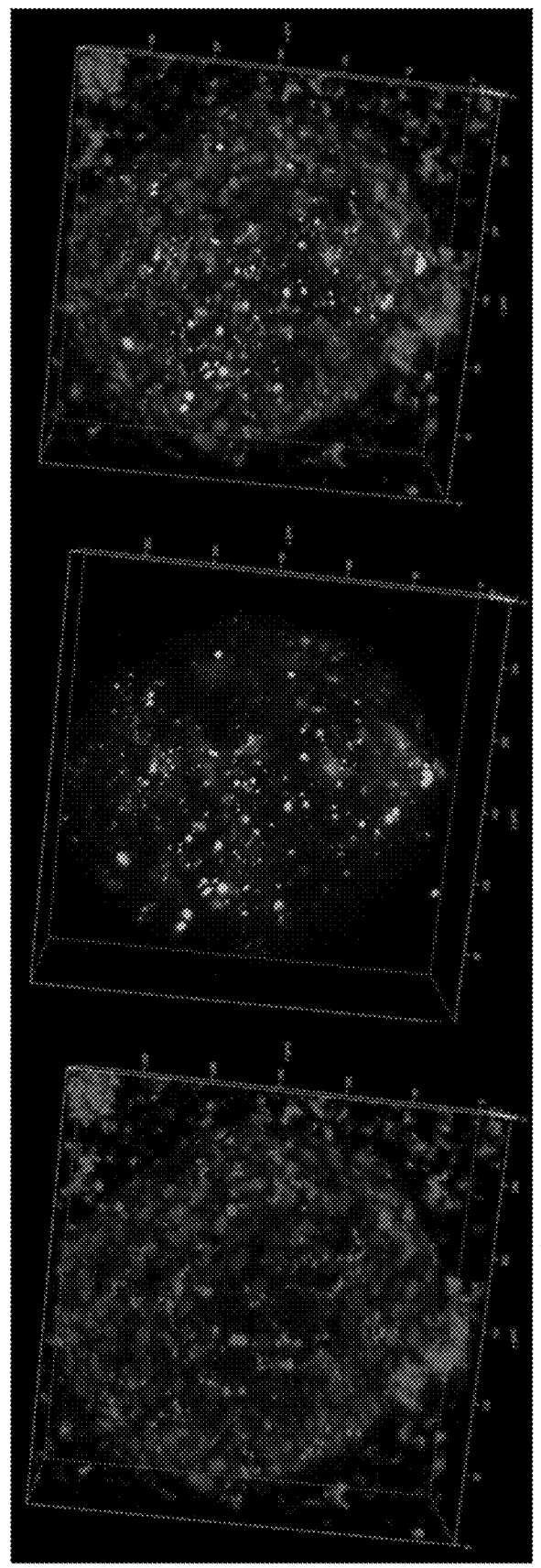
3D-Imaging of GFP-Stained Liver Derived Cell Alignment in Spheroids
Hoechst Fibroblast | GFP Liver Derived Cells | Merged FIGS. 4A-4G, CONTINUED
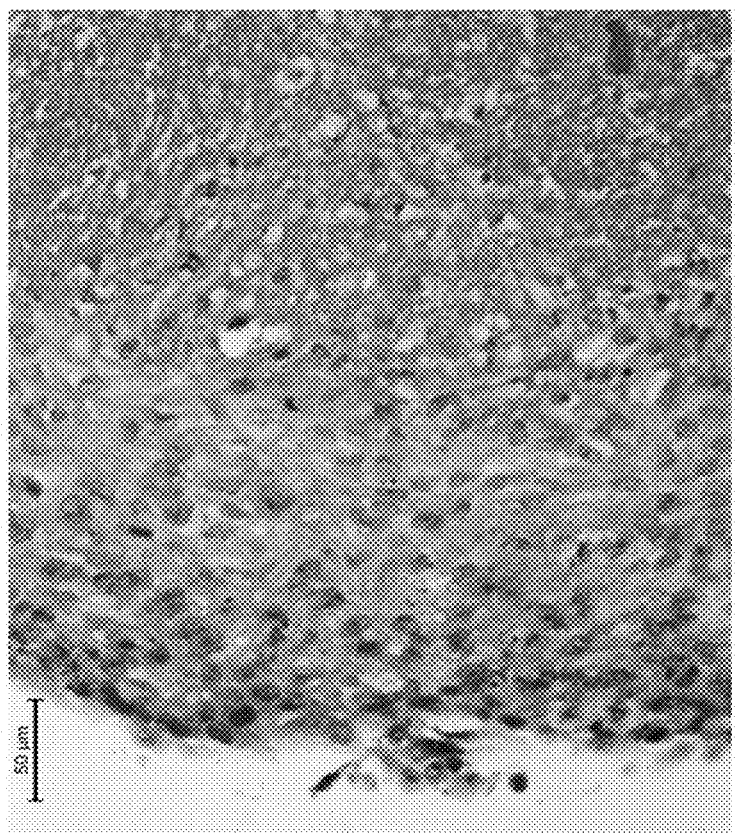
F.
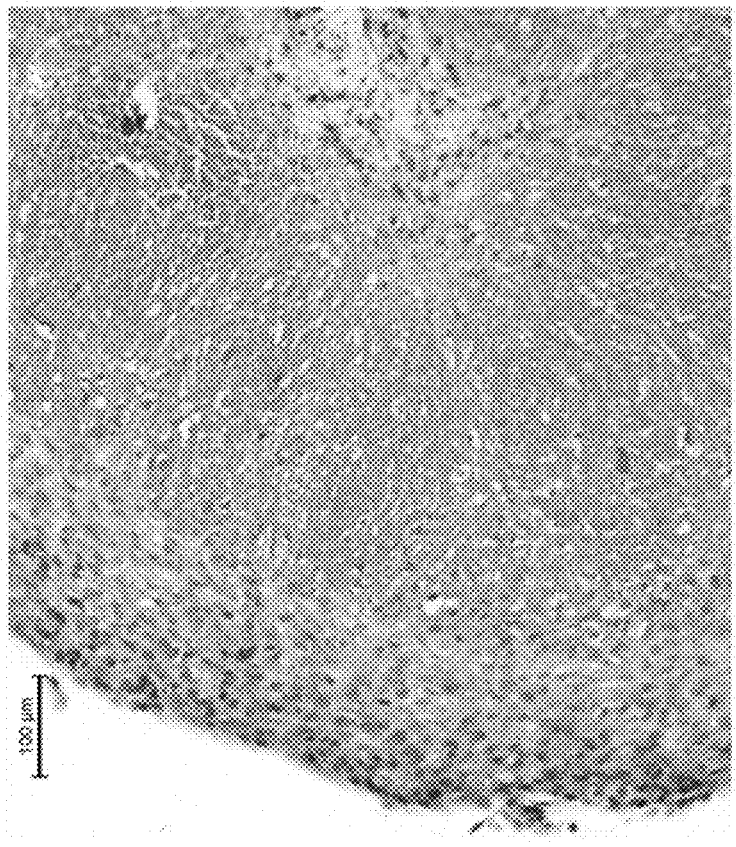
E.

FIGS. 4A-4G, CONTINUED
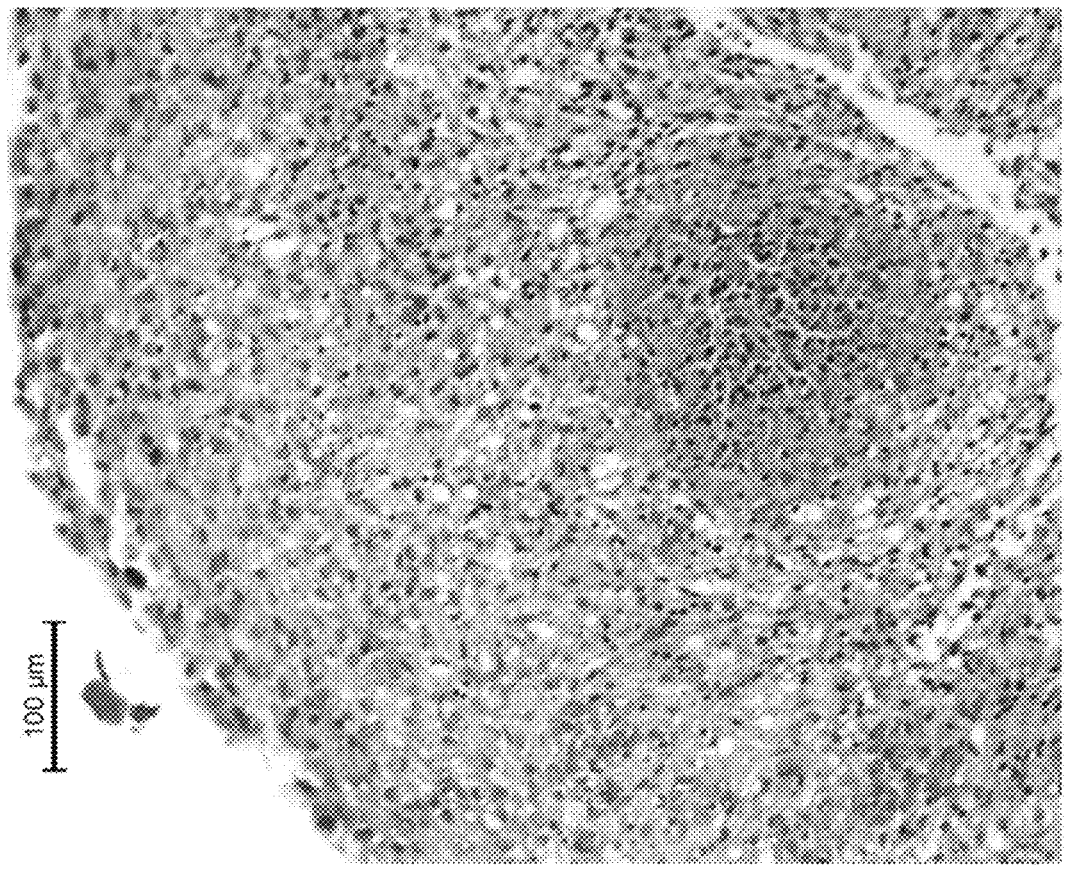
G.

FIG. 19
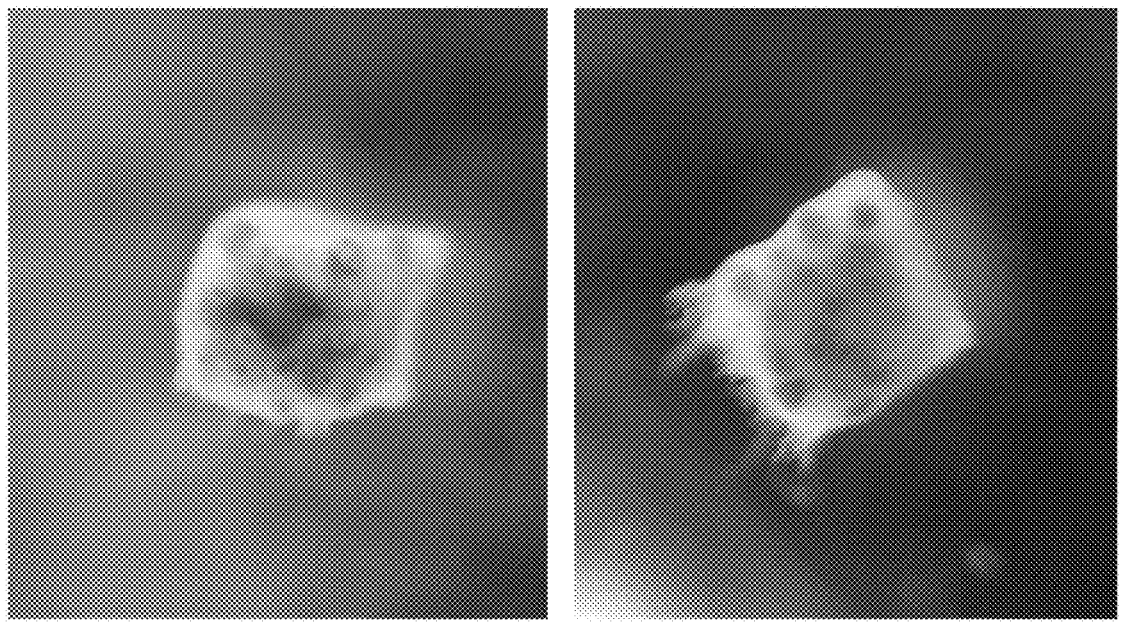
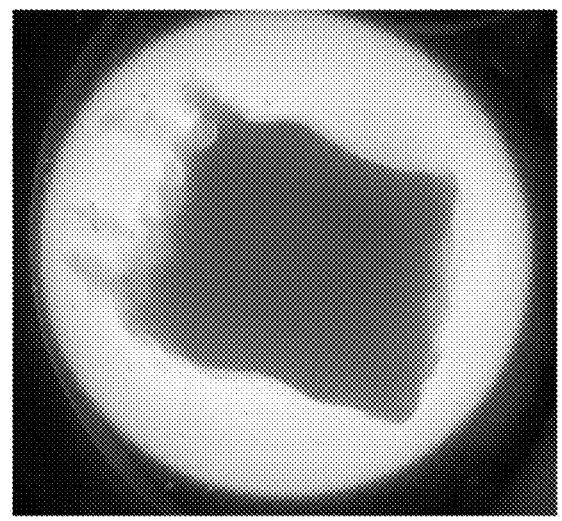
Day 5 — Off Support
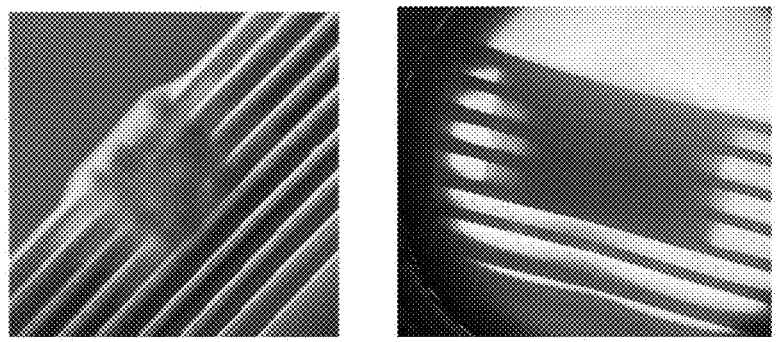
Day 5

FIG. 20 Day 7 Post-Printing – 2 days off support

SCAFFOLD-FREE 3D BIOPRINTING OF PORCINE CELLS

CROSS-REFERENCE TO RELATED APPLICATIONS

This application claims priority to U.S. Provisional Application No. 62/574,809, filed Oct. 20, 2017, which is hereby incorporated by reference herein in its entirety.

STATEMENT REGARDING FEDERALLY SPONSORED RESEARCH

Not applicable.

BACKGROUND

In the United States, more than 116,000 patients are on the waiting list for organ transplantation. Although some alternative treatments exist for kidney and heart failure, such as dialysis and ventricular assist device, respectively, liver transplantation remains the only treatment option for end-stage liver disease. Cross-species transplantation or "xenotransplantation" using genetically engineered pig organs could reduce or eliminate the shortage of donor organs. However, xenotransplant recipients develop a strong immunological response and survival-limiting thrombocytopenia due to species-specific obstacles. In addition, despite advances in genetic engineering and the availability of more than 26 genetically engineered pigs, it is unknown what genetic combination will be best to reduce immunological and coagulation responses following transplantation. Since such obstacles present a critical barrier to progress, there remains a need in the art for efficient, cost-effective alternatives to xenotransplantation.

SUMMARY OF THE DISCLOSURE

Provided herein are synthetic, three-dimensional (3D) bioprinted tissue constructs comprising porcine cells and methods of producing and using the same. The synthetic 3D bioprinted tissue constructs are fabricated by bioprinting spheroids comprising porcine cells on a microneedle mold and fusing the spheroids to form an engineered tissue construct. In some cases, at least a portion of the porcine cells are genetically engineered cells. Also provided are methods of using scaffold-free 3D bioprinted tissue constructs for applications related to drug screening and toxicity screening.

In a first aspect, provided herein is a method for fabricating a synthetic three-dimensional (3D) porcine tissue construct. The method can comprise or consist essentially of providing a predetermined arrangement of microneedles; adding cell spheroids to the microneedles in a computer-controlled manner, wherein the cell spheroids comprise porcine cells of two or more cell types, wherein at least a portion of the porcine cells are genetically engineered; and culturing the spheroids on the microneedles for about 5 days whereby the spheroids fuse to form a synthetic 3D porcine tissue construct comprising genetically engineered porcine cells. In some cases, the method further comprises removing the synthetic 3D porcine tissue construct from the microneedle mold to obtain a scaffold-free synthetic 3D porcine tissue construct comprising genetically engineered porcine cells. The cell spheroids can comprise porcine cells of two or more cell types selected from the group consisting of porcine hepatocytes, liver sinusoidal endothelial cells (LSECs), stellate cells, Kupffer cells, and fibroblasts, and, in such cases, the synthetic 3D porcine tissue construct is a synthetic 3D porcine liver tissue construct. The cell spheroids can comprise porcine cells of two or more cell types selected from the group consisting of porcine pulmonary vascular endothelial cells (CD31$^{+}$ve), pulmonary fibroblasts, pulmonary pneumocytes Type I, and pulmonary pneumocytes Type II and, in such cases, the synthetic 3D porcine tissue construct is a synthetic 3D porcine lung tissue construct. The cell spheroids can comprise porcine cells of two or more cell types selected from the group consisting of porcine corneal endothelial cells, stromal cells, and corneal epithelial cells, and, in such cases, the synthetic 3D porcine tissue construct is a synthetic 3D porcine cornea tissue construct. The cell spheroids can comprise porcine fibroblasts and porcine aortic endothelial cells, and, in some cases, the synthetic 3D porcine tissue construct is a synthetic 3D porcine aortic valve tissue construct. The cell spheroids can comprise porcine cells of two or more cell types selected from the group consisting of porcine alpha cells, beta (islet) cells, fibroblasts, and endothelial cells, and, in such cases, the synthetic 3D porcine tissue construct is a synthetic 3D porcine pancreatic tissue construct. The cell spheroids comprise porcine cells of two or more cell types selected from the group consisting of porcine fibroblasts, endothelial cells, and proximal tubule epithelial cells, and wherein the synthetic 3D porcine tissue construct is a synthetic 3D porcine kidney tissue construct.

In another aspect, provided herein is a synthetic 3D porcine tissue construct obtained according to any one of the methods of this disclosure.

In a further aspect, provided herein is a composition comprising a 3D scaffold-free porcine tissue obtained according to the steps of: bioprinting cell spheroids comprising genetically engineered porcine cells onto a predetermined arrangement of microneedles; culturing the bioprinted cell spheroids for about 5 days whereby the bioprinted cell spheroids fuse to form a three-dimensional porcine tissue construct; and removing the porcine tissue construct from the microneedles to obtain a 3D scaffold-free porcine tissue construct. The cell spheroids can comprise a plurality of porcine cells of two or more cell types selected from the group consisting of porcine hepatocytes, porcine liver sinusoidal endothelial cells (LSECs), and porcine fibroblasts, and, in such cases, the 3D scaffold-free porcine tissue is a 3D scaffold-free porcine liver tissue. The cell spheroids can comprise porcine cells of two or more cell types selected from the group consisting of porcine pulmonary vascular endothelial cells (CD31$^{+}$ve), pulmonary fibroblasts, pulmonary pneumocytes Type I, and pulmonary pneumocytes Type II, and, in such cases, the synthetic 3D porcine tissue construct is a synthetic 3D porcine lung tissue construct. The cell spheroids can comprise porcine cells of two or more cell types selected from the group consisting of porcine corneal endothelial cells, stromal cells, and corneal epithelial cells, and, in such cases, the synthetic 3D porcine tissue construct is a synthetic 3D porcine cornea tissue construct. The cell spheroids comprise porcine fibroblasts and porcine aortic endothelial cells, and wherein the synthetic 3D porcine tissue construct is a synthetic 3D porcine aortic valve tissue construct. The cell spheroids can comprise porcine cells of two or more cell types selected from the group consisting of porcine alpha cells, beta (islet) cells, fibroblasts, and endothelial cells, and, in such cases, the synthetic 3D porcine tissue construct is a synthetic 3D porcine pancreatic tissue construct. The cell spheroids can comprise porcine cells of two or more cell types selected from the group consisting of porcine fibroblasts, endothelial cells, and proximal tubule epithelial cells, and, in such cases, the synthetic 3D porcine tissue construct is a synthetic 3D porcine kidney tissue construct.

In another aspect, provided herein is a method of testing a compound, the method comprising the compound to a 3D scaffold-free porcine tissue construct obtained according to any one of the methods of this disclosure and examining the effect of the compound on cells within the construct.

BRIEF DESCRIPTION OF THE DRAWINGS

This patent application file contains at least one drawing executed in color. Copies of this patent or patent application publication with color drawings will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein.

Urea concentration in media samples across 14 days of HC:HSC (2.5:1 ratio), HSC (a). Real-time PCR analysis of mRNA transcription in spheroids. Combination spheroids expressed higher levels of both marker genes (b).

Figure 17:
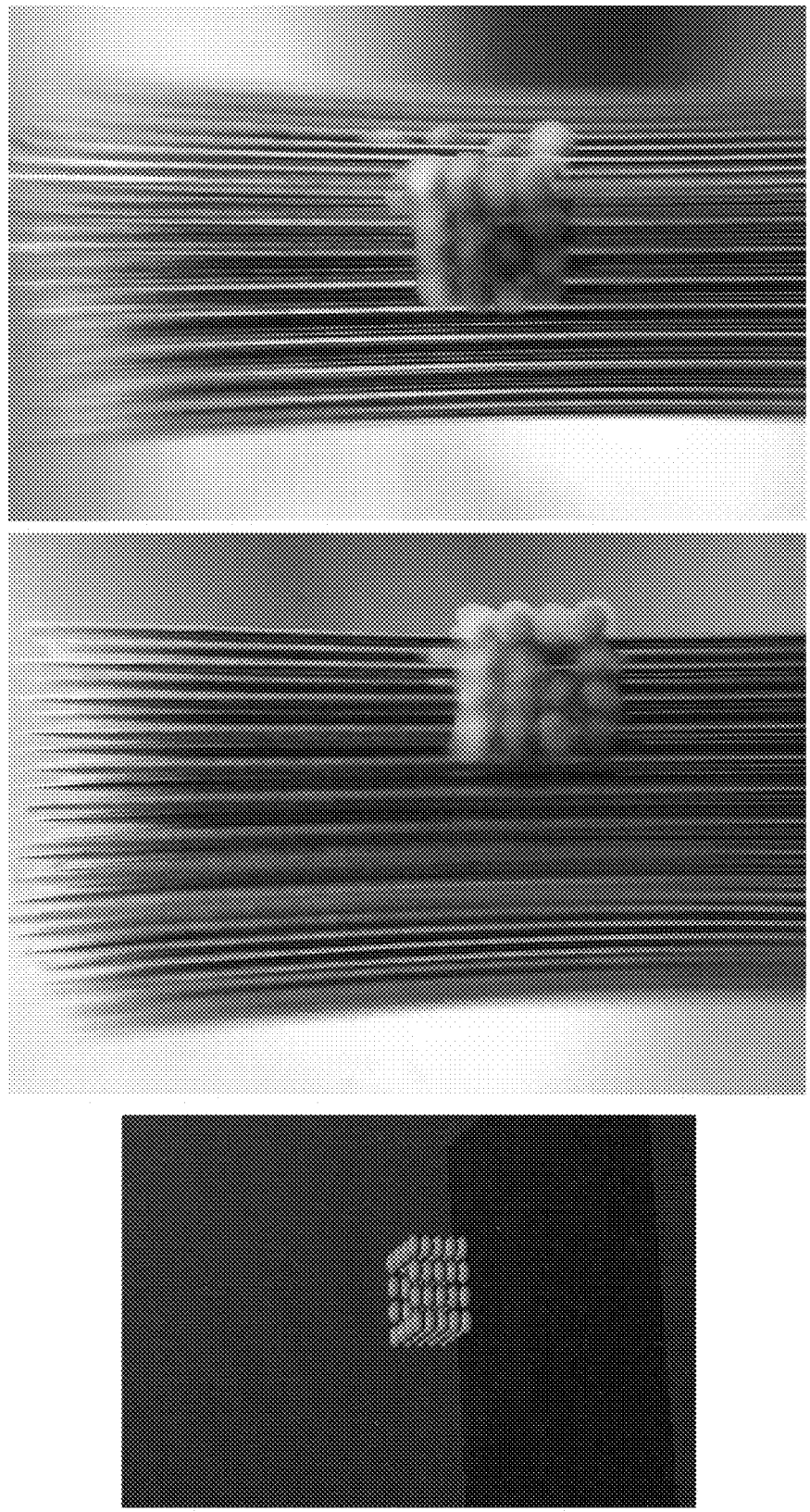

FIG. 17 presents images showing scaffold-free bioprinted lung spheroids immediately following bioprinting.

Figure 18:
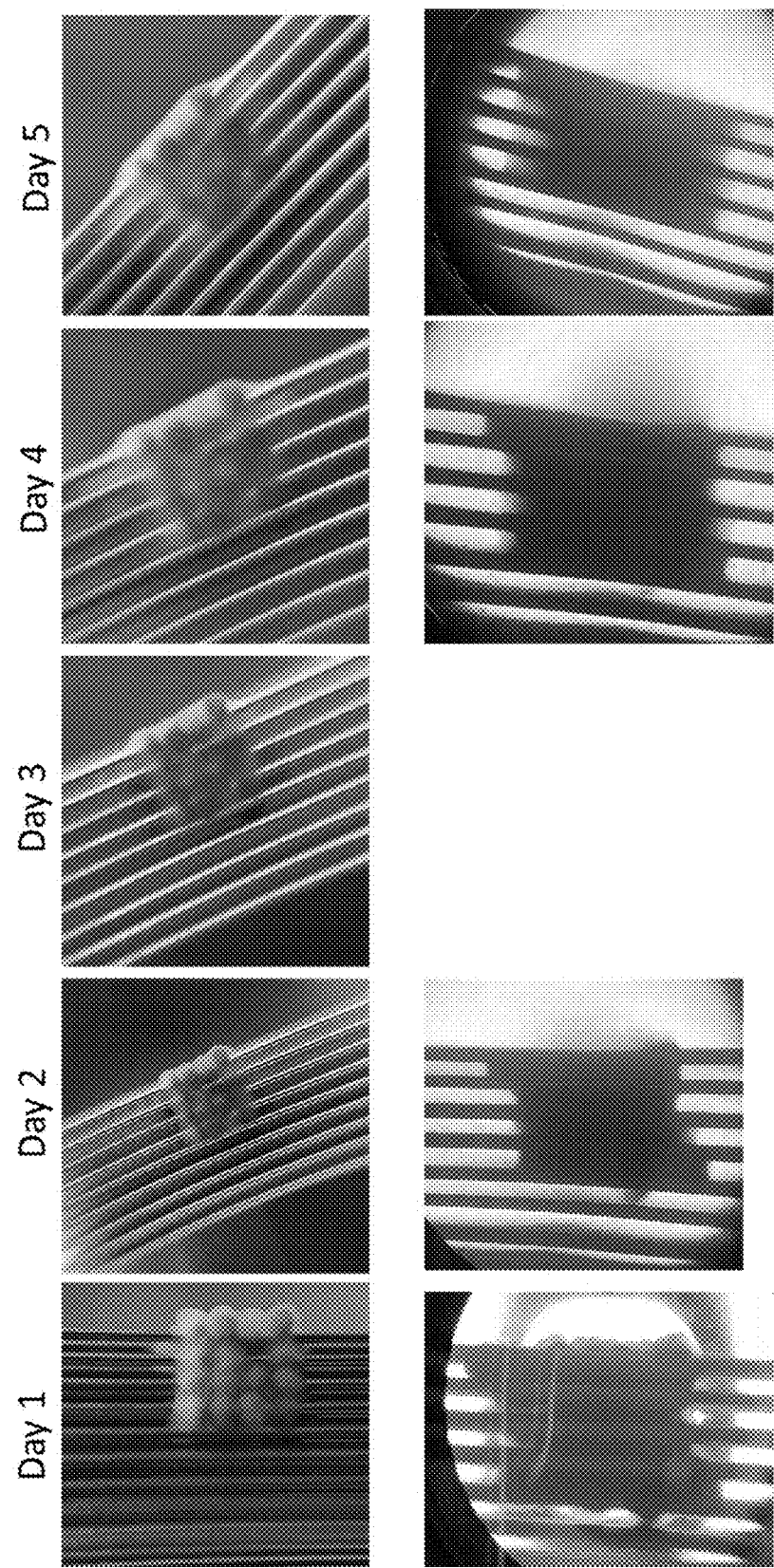

FIG. 18 presents images showing scaffold-free bioprinting of lung spheroids on post-printing days 1, 2, 3, 4, and 5.

FIG. 19 presents images of a scaffold-free bioprinted lung construct on post-printing day 5 (left images) and after removal from the support (right images).

Figure 20:
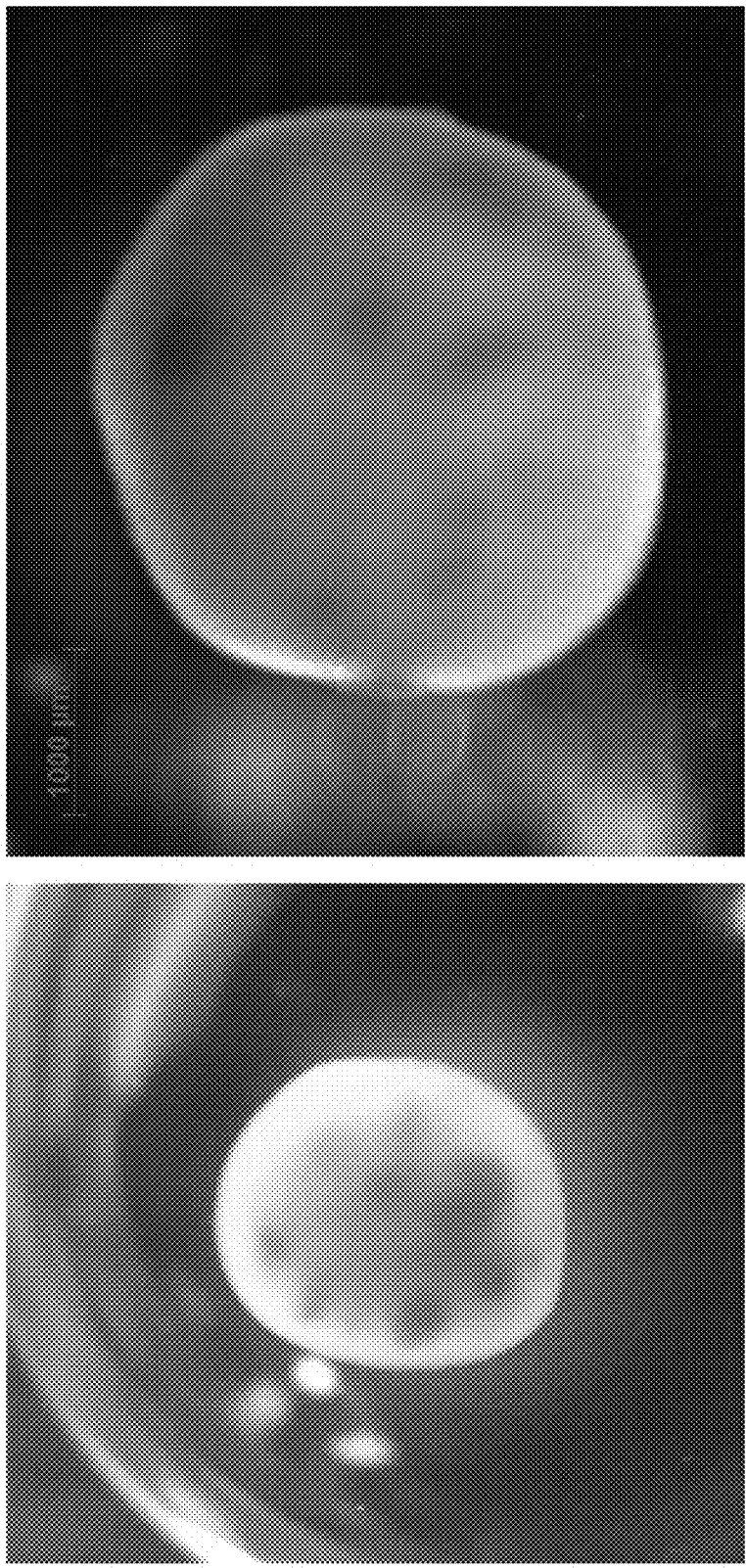

FIG. 20 presents images of a scaffold-free bioprinted lung construct on post-printing day 7 and two days after removal from the support.

Figure 21:
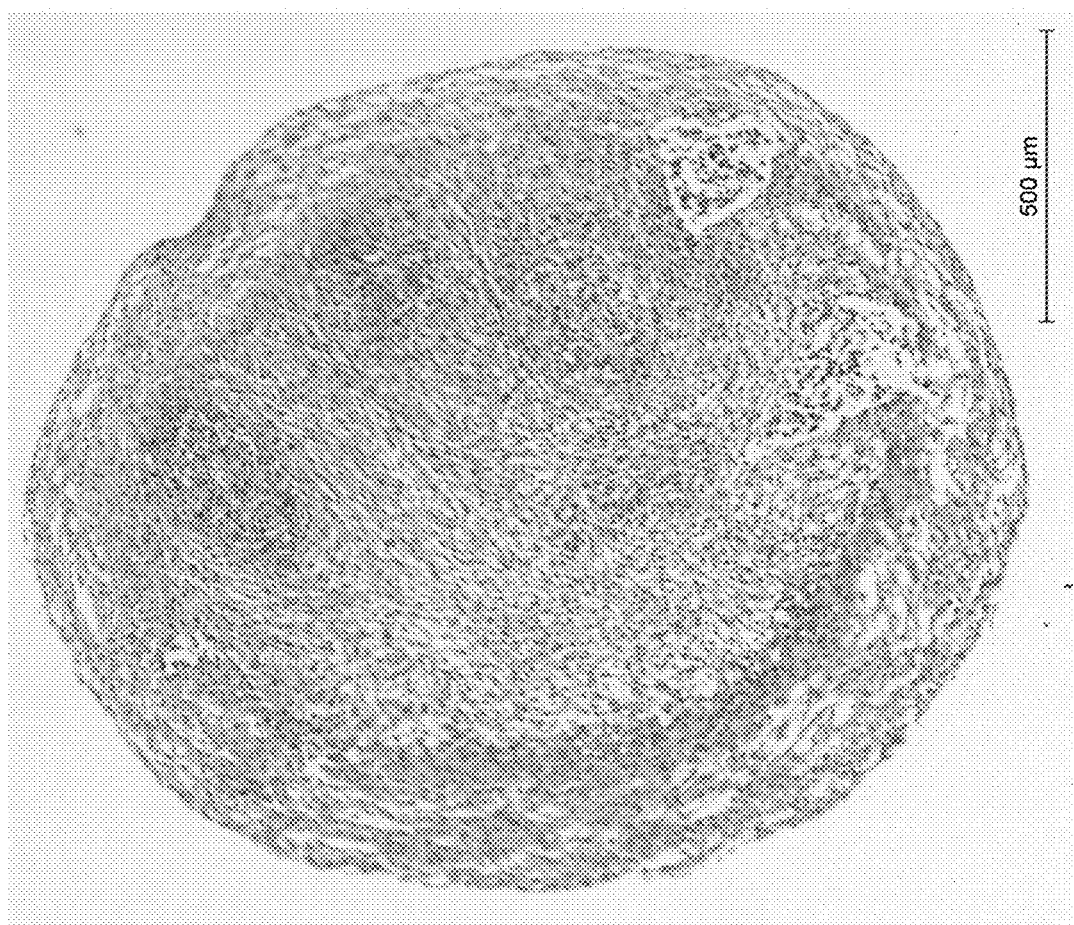

FIG. 21 is an image of H&E (Haemotoxylin and Eosin) stained bioprinted lung construct.

Figure 22:
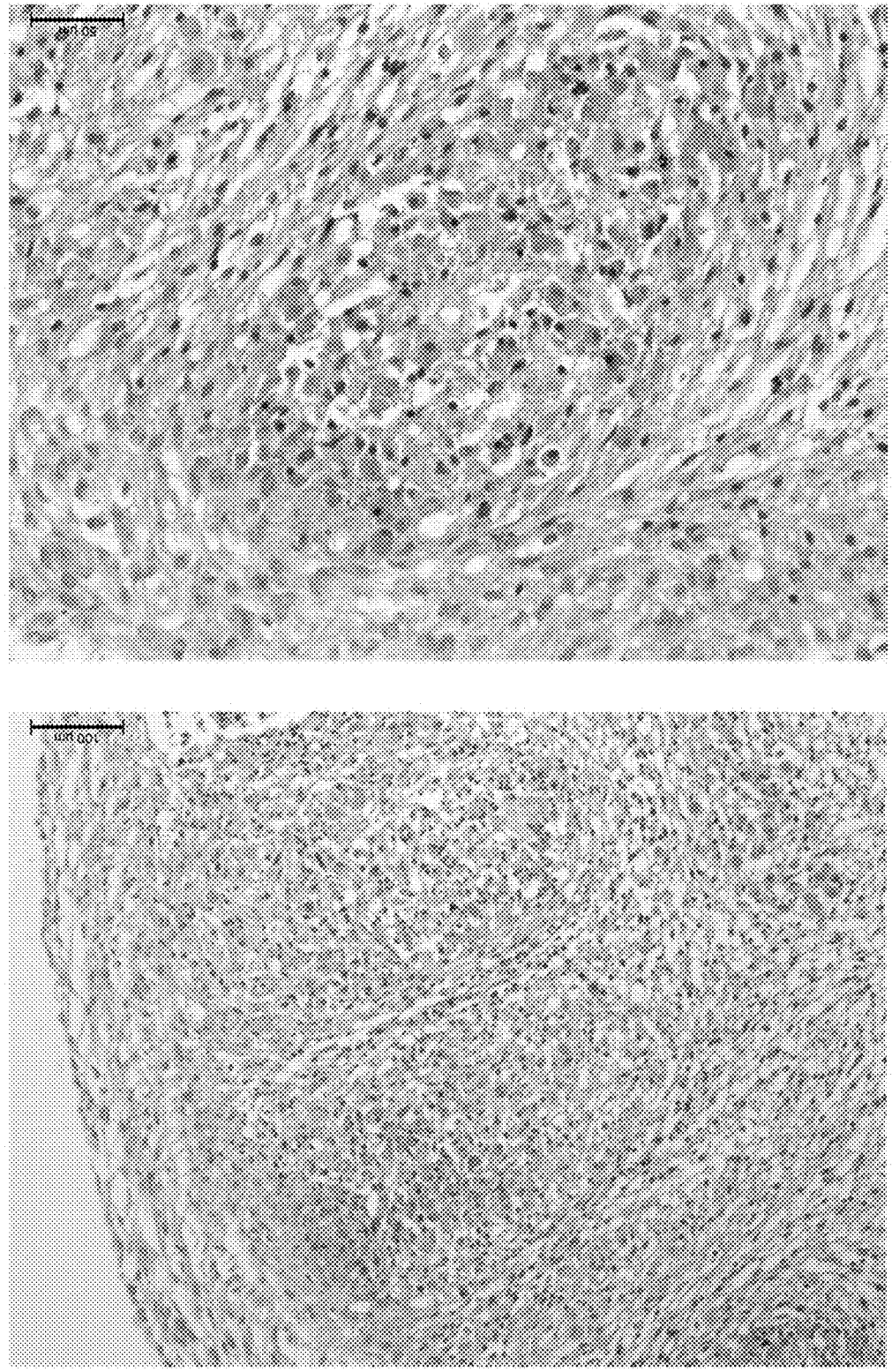

FIG. 22 presents images of H&E stained bioprinted lung construct.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The methods and systems provided herein are based at least in part on the inventors' development of bioprinted porcine tissue structures that are multicellular three-dimensional (3D) structures generated with porcine cells. The bioprinted tissue structures are fabricated by 3D bioprinting spheroids comprising porcine cells and fusing the spheroids to form a scaffold-free engineered structure.

Among the advantages of the methods and systems provided herein, scaffold-free 3D bioprinted constructs of this disclosure provide a more reliable model than standard in vitro models and eliminate the need for pig cloning for each genetic modification, thus providing a faster and cheaper alternative to standard pig-to-human in vivo models of xenotransplantation. Indeed, the bioprinting methods described herein provide an improved model in which to study genetic modifications and combinations in a time- and budget-efficient manner. Exemplary uses of the 3D bioprinted tissue constructs provided herein include but are not limited to recapitulating porcine tissues as a model for studying human immune responses and coagulation responses to pig-to-human xenotransplantation.

Accordingly, in a first aspect, provided herein is a method for bioprinting a synthetic, three-dimensional (3D), scaffold-free porcine tissue construct comprising genetically engineered porcine cells. As used herein, the term "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated or semi-automated, computer-aided, three-dimensional prototyping device (e.g., a bioprinter). The term "scaffold-free" as used herein is intended to imply that no scaffold (e.g., synthetic scaffold, non-synthetic scaffold, or any type of pre-formed scaffold) forms an integral part of the engineered tissue at the time of use, either having been removed or remaining as an inert component of the bioprinted tissue. The terms "scaffold-free" is used interchangeably herein with "scaffoldless" and "free of pre-formed scaffold." Suitable bioprinters include, without limitation, the Regenova Scaffold-Free 3D Bioprinter by Cysfuse Biomedical (Tokyo, Japan). Other suitable bioprinters are commercially available, such as Bio X 3D Bioprinter by Cellink (Boston, Mass.).

In certain embodiments, the bioprinting method for fabricating an engineered three-dimensional (3D) porcine tissue construct comprises providing a predetermined arrangement of microneedles as a template for forming the engineered three-dimensional porcine tissue; adding porcine cell spheroids to the microneedles in a computer-controlled manner, wherein the porcine cell spheroids comprise two or more cell types; and culturing the spheroids on the microneedle mold for about 5 days whereby the spheroids fuse to form a three-dimensional, scaffold-free porcine liver tissue. In certain embodiments, at least one porcine cell type is a genetically engineered porcine cell.

In some cases, the method further comprises removing the three-dimensional porcine tissue from the microneedles to obtain an engineered scaffold-free 3D porcine tissue construct. In some cases, a robotic platform is to "bioprint" spheroids into predesigned contiguous structures. The microneedles provide temporary support as the spheroids fuse into cellular aggregates and synthesize their own extracellular matrix, thereby attaining the needed structural robustness to be removed from the microneedles as scaffold-free tissue constructs.

The spheroids comprise porcine cells. In some cases, the spheroids comprise heterologous mixture of porcine cells. In some cases, porcine cell spheroids comprise two or more cell types. In some cases, the spheroids comprise two porcine cell types. In other cases, the spheroids comprise three or more porcine cell types. Appropriate cell types for the spheroids will differ based on the tissue type to be produced according to the methods of this disclosure. For example, to produce a synthetic 3D porcine liver tissue, cell spheroids preferably comprise porcine liver cell types such as hepatocytes, liver sinusoidal endothelial cells (LSECs), hepatic stellate cells (HSCs), cholangiocytes, and fibroblasts. To produce a synthetic 3D cornea-like tissue, the cell spheroids preferably comprise porcine cells such as corneal endothelial cells, stromal cells, and corneal epithelial cells. To produce a synthetic 3D aortic valve-like tissue, the cell spheroids comprise cell types such as porcine fibroblasts and porcine aortic endothelial cells. To produce a synthetic 3D pancreas-like tissue, the cell spheroids preferably comprise cells such as porcine alpha cells, beta (islet) cells, fibroblasts, and endothelial cells. To produce a synthetic 3D kidney-like tissue, the cell spheroids preferably comprise cells such as porcine fibroblasts, endothelial cells, proximal tubule epithelial cells, and other renal cells. To produce a synthetic 3D lung-like tissue, the cells spheroids preferably comprise porcine pulmonary vascular endothelial cells (CD31$^{+}$ve), pulmonary fibroblasts, and pulmonary pneumocytes.

Spheroids for use according to the methods provided herein can be produced by any appropriate method of aggregating cultured cells. In certain embodiments, cells are cultured on low-adhesion or non-adhesive plates under conditions that promote spontaneous aggregation into spheroids. Spheroid size is determined, at least in part, by cell number and culture time. In some cases, about 10,000 to 50,000 cells (e.g., about 10,000, about 20,000, about 30,000, about 40,000, about 50,000) of each type are used to prepare spheroids have a diameter of approximately 400-600 µm. In some cases, a total of 35,000-40,000 cells are seeded on a non-adhesive culture plates under conditions that promote spontaneous aggregation into spheroids. In other cases, the number of cells of each type can be increased or decreased as necessary used to generate spheroids have a diameter of approximately 400-600 µm (e.g., about 400, 450, 500, 550, 600 µm, inclusive) in about two to about three days in culture.

Figure 5:
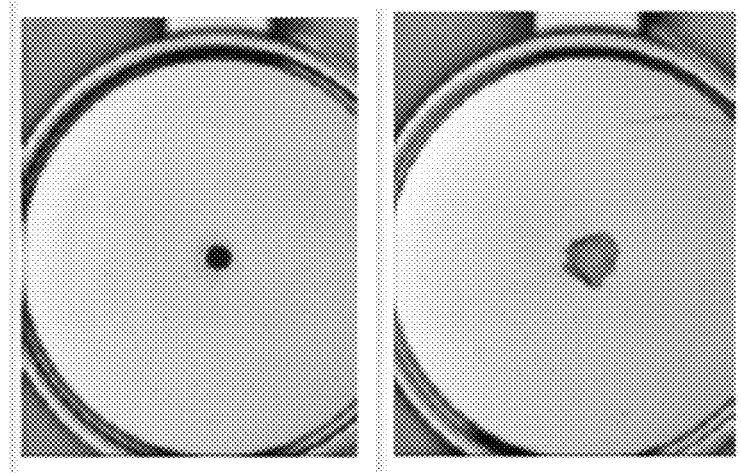
FIG. 5 shows images of (top) a well-formed spheroid inside a 96-well plate, and (bottom) an aggregate of cells that failed to form a spheroid. In this example, the cells are mouse hepatocytes.
Figure 6:
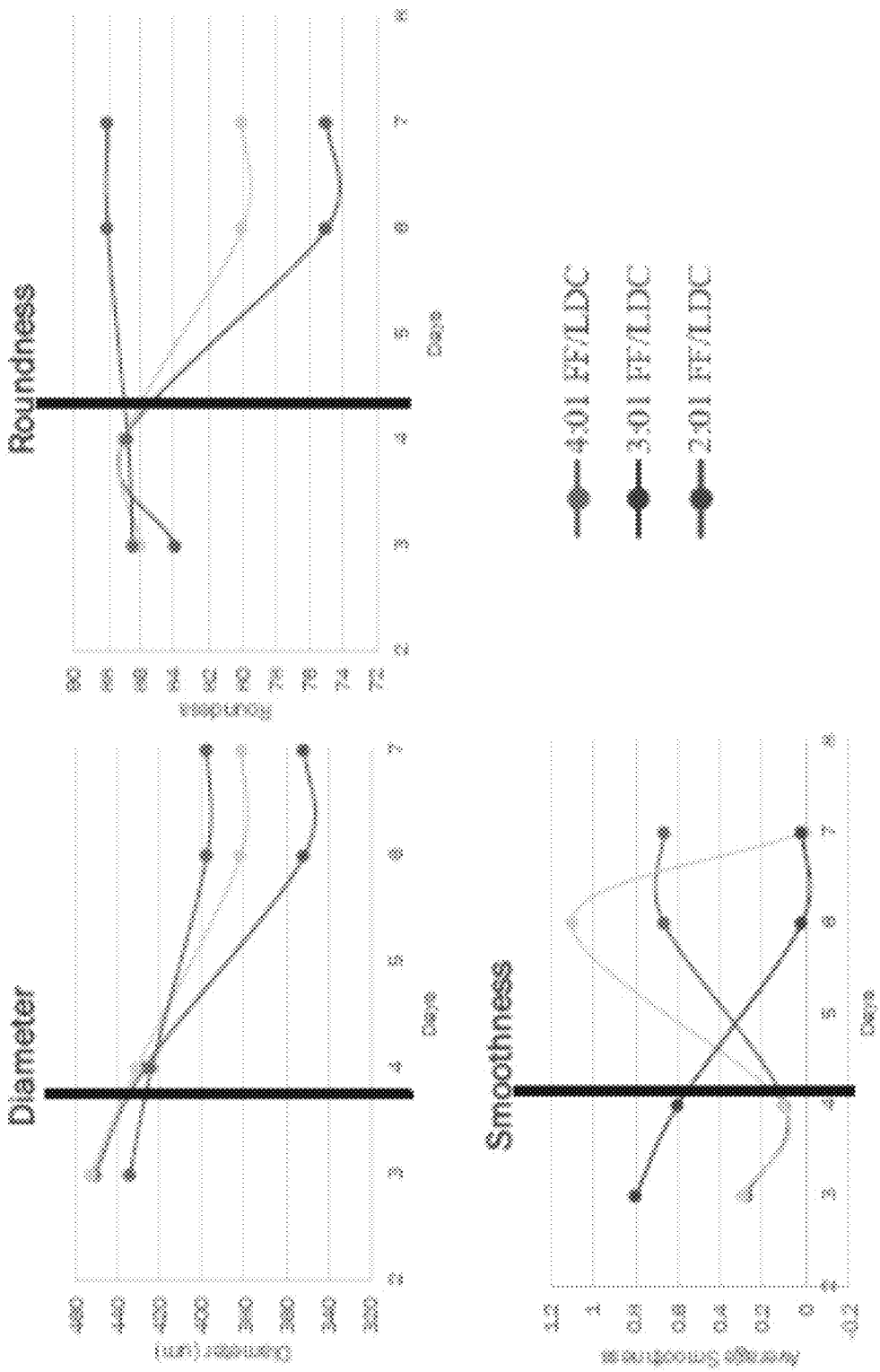
FIG. 6 presents graphs demonstrating spheroid characteristics when prepared using different ratios of fibroblasts and liver-derived cells.
Figure 7:
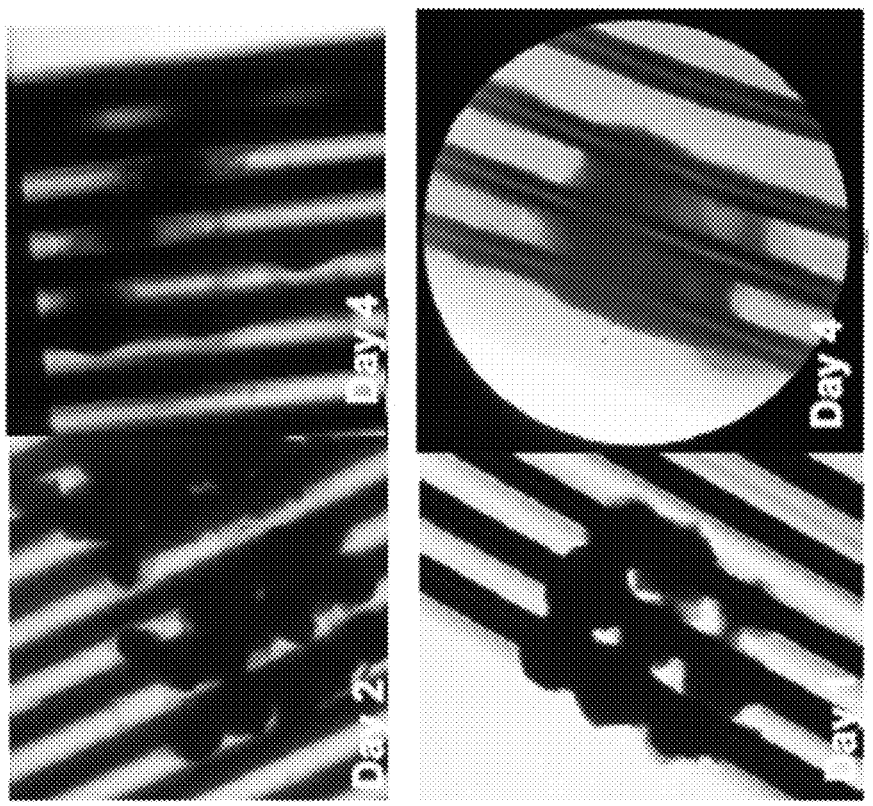
FIG. 7 presents images of tissue constructs comprising bioprinted spheroids. (top) Spheroids printed at 4:1 ratio of fibroblasts to liver-derived cells, using 32,000 cells. (bottom) Spheroids printed at 10:1 ratio of fibroblasts to liver-derived cells, using 40,000 cells.
Figure 8:
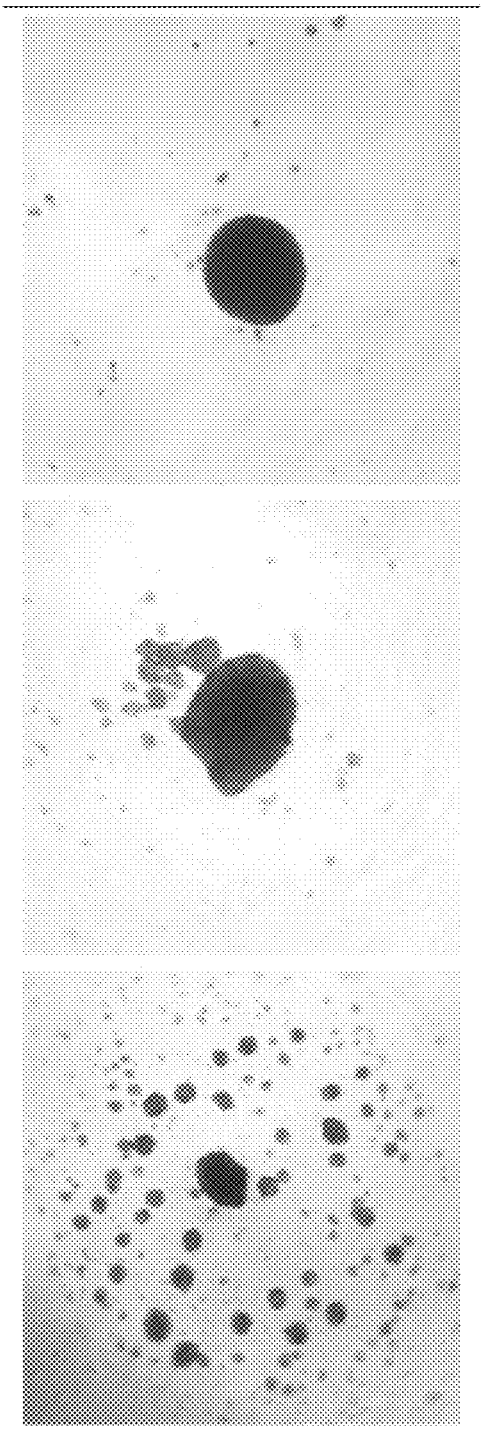
FIG. 8 presents images of spheroid formation (comprising fibroblasts, hepatocytes, and liver-derived cells at a ratio of 2:1:0.1) on days 1, 2, and 5.
Figure 9:
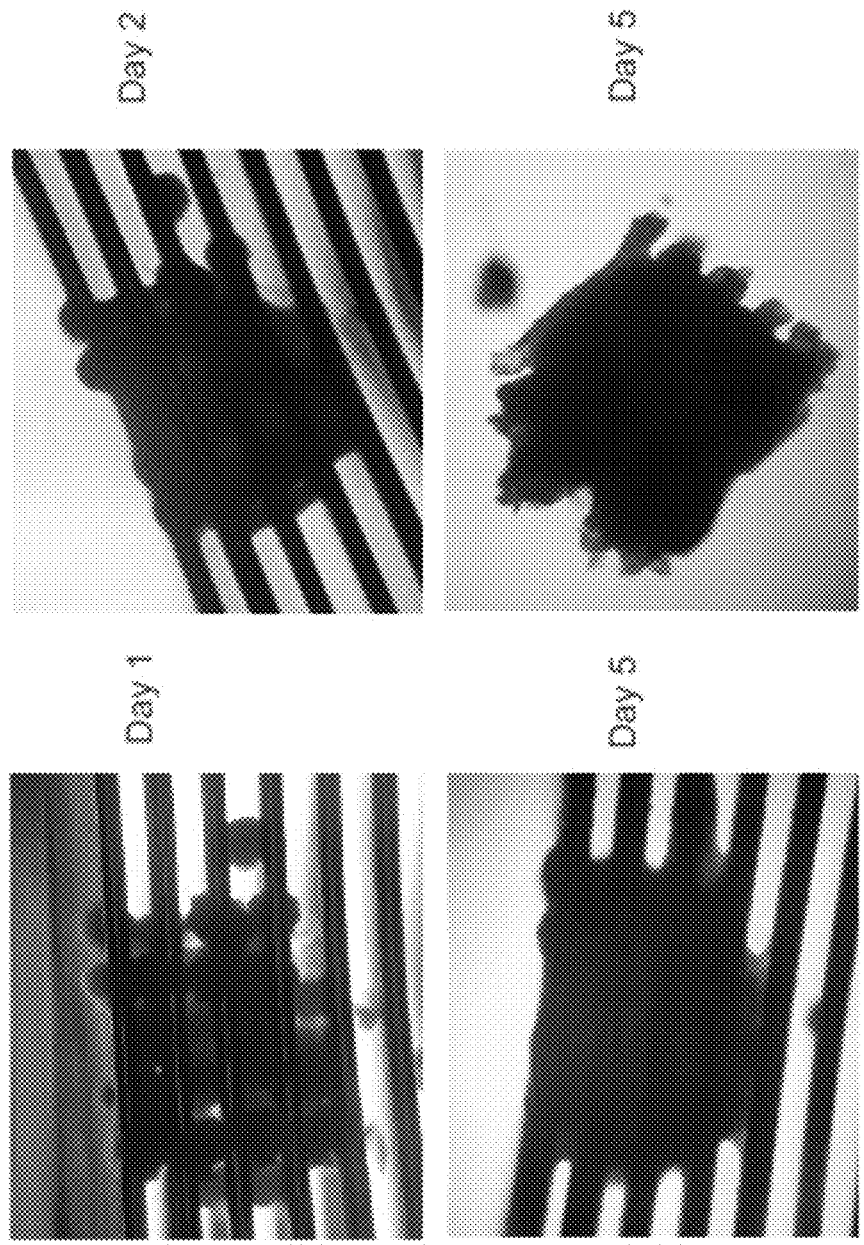
FIG. 9 presents images of bioprinted 3-cell spheroids (comprising fibroblasts, hepatocytes, and liver-derived cells at a ratio of 2:1:0.1) on days 1, 2, and 5.
Figures 10A, 10B:
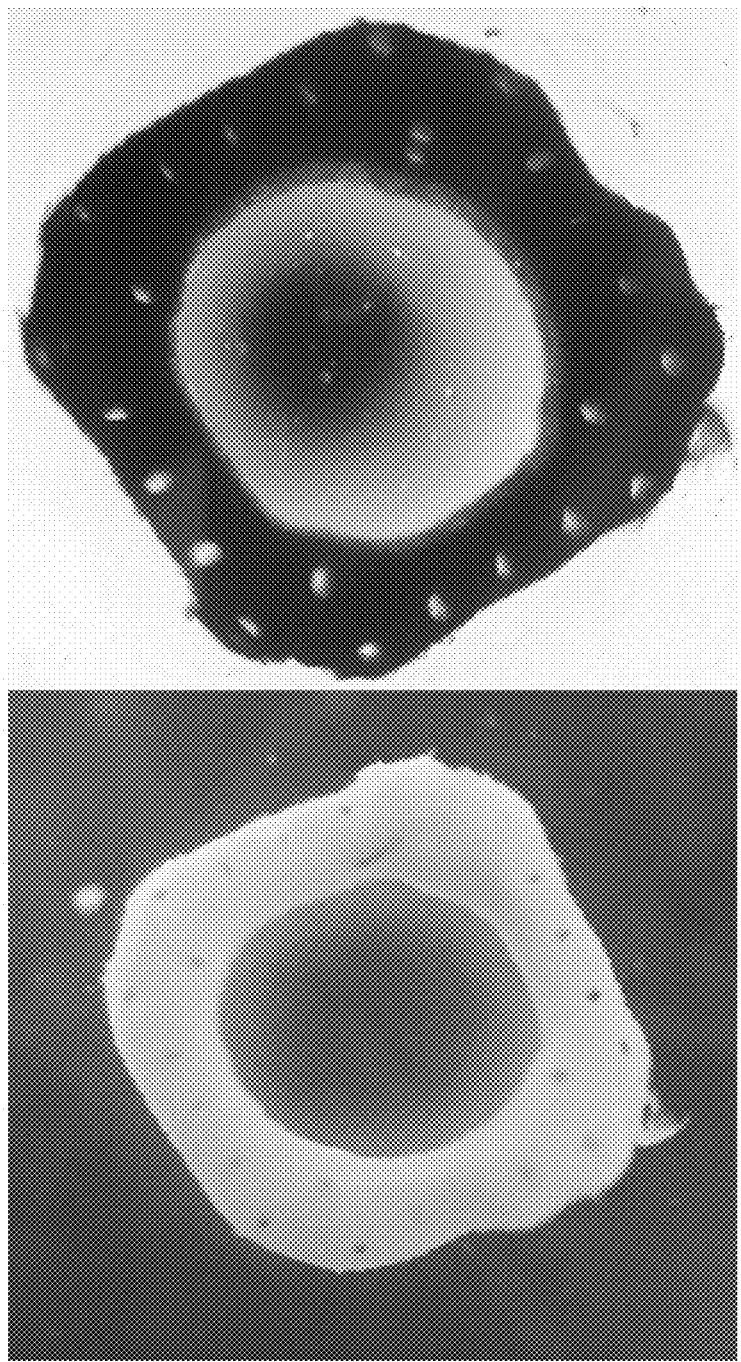
FIGS. 10A-10B. Scaffold-free 3D-bioprinted genetically-engineered porcine liver model 1 week after bioprinting. Visible with naked eye (A), under microscope (B). Small holes on the 3D-construct represent holes of micro-needles.

Spheroids are made using different ratios of the two, three, four, or more cell types. For example, referring to FIG. 6, a ratio of 4:1, 5:1, or 10:1 of fibroblasts:LSECs can be used. Referring to FIGS. 8 and 9, spheroids comprising three porcine liver cell types can be produced by seeding fibroblasts, hepatocytes, and liver-derived cells at a ratio of 2:1:0.1. It will be understood by those having ordinary skill in the art that ratios of cell types may vary based on the number of porcine cell types, culture conditions, spheroid size, cell viability, and other variable. After seeding two, three, four, or more cell types on the culture plates, about 48 to about 72 hours incubation are required for formation of strong, round spheroids suitable for bioprinting. See, for example, exemplary spheroids in FIGS. 5 and 8.

As used herein, the terms "synthetic" and "engineered" are used interchangeably and refer to a non-naturally occurring tissue material that has been created or modified by the hand of man (e.g., bioprinting cells in a predetermined arrangement) or is derived using such material (e.g., an implant or other device comprising the synthetic material). In some cases, cells or cell spheroids used to produce the synthetic tissue material are wild-type cells or may contain one or more synthetic or genetically engineered nucleic acids (e.g., a nucleic acid containing at least one artificially created insertion, deletion, inversion, or substitution relative to the sequence found in its naturally occurring counterpart). Cells comprising one or more synthetic or engineered nucleic acids are considered to be an engineered cell. As used herein, the terms "tissue" and "tissue construct" refer to aggregates of cells.

In some cases, a 3D porcine tissue construct produced according to the methods described herein may comprise recombinant or genetically-modified cells in place of or in addition to unmodified or wild-type ("normal") cells. For example, it can be advantageous in some cases to include recombinant/genetically-modified cells that produce recombinant cell products, growth factors, hormones, peptides or proteins (e.g., detectable reporter proteins) for a continuous amount of time or as needed such as, for example, when biologically, chemically, or thermally signaled due to the conditions present in culture. Procedures for producing genetically modified cells are generally known in the art, and are described in Sambrook et al, *Molecular Cloning, A Laboratory Manual*, Cold Spring Harbor Press, Cold Spring Harbor, N.Y. (1989), incorporated herein by reference.

In some cases, at least a portion of porcine cells used to form a porcine cell spheroid are genetically modified (genetically engineered) porcine cells. As used herein, the term "genetic modification" and its grammatical equivalents can refer to one or more alterations of a nucleic acid, e.g., the nucleic acid within the genome of an organism or cells thereof. For example, genetic modification can refer to alterations, additions, and/or deletion of genes. A genetically modified cell can also refer to a cell with an added, deleted and/or altered gene. In some cases, cells isolated from a wild-type (not genetically modified) non-human animal such as a pig or another mammal are genetically modified for use according to a method provided herein. In some cases, the genetically modified cell is a cell isolated from a genetically modified non-human animal (e.g., a genetically modified pig). A genetically modified cell from a genetically modified non-human animal can be a cell isolated from such genetically modified non-human animal. In some cases, a genetically modified cell of a non-human animal can comprise reduced expression of one or more genes as compared to a non-genetically modified counterpart animal. A non-genetically modified counterpart animal can be an animal substantially identical to the genetically modified animal but without genetic modification in the genome. For example, a non-genetically modified counterpart animal can be a wild-type animal of the same species as the genetically modified animal.

In some cases, genetic modifications are produced using a form of gene editing. The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease). In some cases, gene editing is performed using a CRISPR/cas system (e.g., a type II CRISPR/cas system). For example, a CRISPR/cas system can be used to reduce expression of one or more genes in cells of a spheroid. In some cases, the protein expression of one or more endogenous genes is reduced using a CRISPR/cas system. In other cases, a CRISPR/Cas system can be used to perform site specific insertion. For example, a nick on an insertion site in the genome can be made by CRISPR/cas to facilitate the insertion of a transgene at the insertion site. Other methods of making genetic modifications suitable for use according to the methods provided herein include but are not limited to somatic cell nuclear transfer (SCNT) and introduction of a transgene. As used herein, the term "transgene" refers to a gene or genetic material that can be transferred into an organism or a cell thereof. Procedures for obtaining recombinant or genetically modified cells are generally known in the art, and are described in Sambrook et al, *Molecular Cloning, A Laboratory Manual*, Cold Spring Harbor Press, Cold Spring Harbor, N.Y. (1989), incorporated herein by reference.

To study the effects of various genetic modifications on human responses to porcine tissue transplants, it will be advantageous in some cases to use genetically modified cells in which the cells are modified for reduced expression of xenoreactive antigens. For example, porcine liver cell types (e.g., hepatocytes, fibroblasts, HSCs, liver sinusoidal endothelial cells, cholangiocytes) can be genetically modified using a CRISPR/Cas system to selectively reduce expression of porcine tetraspanins pCD37 and pCD81 relative to a non-genetically modified cell. In some cases, cells are genetically modified using CRISPR/Cas for reduced expression of one or more major histocompatibility complex (MHC) molecules (e.g., MHC I molecules and/or MHC II molecules) as compared to a non-genetically modified counterpart animal. In some cases, porcine cells are engineered to genetically modify (e.g., mutate) or modulate (e.g., increase, decrease) the expression of genes such as pGGTA1, pCMAH, pB4GalNT2, porcine tetraspanin pCD37, porcine tetraspanin pCD81, human (h) CD46, hCD55, human thrombomodulin, CD46 (membrane co-factor protein), CD55 (decay-accelerating factor), CD59 (protectin or membrane inhibitor of reactive lysis), Human H-transferase (e.g., for expression of blood type 0 antigen), Endo-β-galactosidase C (e.g., for reduction of Gal antigen expression), α1,3-galactosyltransferase, Cytidine monophosphate-N-acetylneuraminic acid hydroxylase (CMAH), β1,4-N-acetylgalactosaminyltransferase (β4GalNT2) (e.g., β4GalNT2 knock out), CIITA-DN (e.g., MHC class II transactivator knockdown, resulting in swine leukocyte antigen class II knockdown), Class I MHC-knockout (MHC-IKO), HLA-E/human β2-microglobulin (e.g., to inhibit human natural killer cell cytotoxicity), Human FAS ligand (CD95L), Human N-acetylglucosaminyltransferase III (GnT-III) gene, Porcine CTLA4-Ig (cytotoxic T lymphocyte antigen 4 or CD152), Human TRAIL (tumour necrosis factor-α-related apoptosis-inducing ligand), von Willebrand factor (vWF), Human tissue factor pathway inhibitor (TFPI), Human endothelial protein C receptor (EPCR), Human ectonucleoside triphosphate diphosphohydrolase-1 (CD39), Human tumour necrosis factor-α-induced protein 3 (A20), Human haem oxygenase-1 (HO-1), Human CD47 (species-specific interaction with SIRP-α inhibits phagocytosis), Porcine asialoglycoprotein receptor 1 (ASGR1) (e.g., to decrease platelet phagocytosis), Human signal regulatory protein-α (SIRPα) (e.g., to decrease platelet, phagocytosis by 'self' recognition).

Cells for spheroids can be generated, harvested, and/or cultured according to any appropriate protocols. In some cases, cells for spheroids can be generated from enzymatically dissociated (e.g., trypsin treated) and/or mechanically dissociated tissues of interest, from cell lines, or from stem cells (e.g., directed differentiation of stem cells into a cell type of interest). Porcine adult liver-derived cells (LDCs) can be isolated and/or cultured as described in WO/2014/066505.

Any appropriate method(s) can be used to assay spheroids and 3D scaffold-free porcine tissue constructs for viability and tissue-specific metabolic activity. For example, liver tissue constructs and spheroids comprising liver cells can be tested for urea and albumin production.

Any appropriate method or methods can be used to confirm uniformity and the presence or absence of certain components in a 3D porcine tissue construct provided herein. Suitable methods for detecting the presence or absence of biological markers are well known in the art and include, without limitation, immunohistochemistry, qRT-PCR, RNA sequencing, and the like for evaluating gene expression at the RNA level. In some cases, methods such as immunohistochemistry are used to detect and identify cell types or biomolecules within a 3D porcine liver tissue construct. For example, whole porcine liver tissue constructs or portions thereof can be stained for specific differentiation markers by immunohistochemistry. In some cases, it will be advantageous to perform dual-label immunofluorescence to assess the relative expression of individual marker proteins or to detect multiple progenitor or differentiated cell types within a construct. Appropriate primary and secondary antibodies are known and available to those practicing in the art. In addition, microarray technology or nucleic acid sequencing (e.g., RNA sequencing) can be used to obtain gene expression profiles for synthetic 3D porcine liver tissue constructs. Quantitative methods for evaluating expression of markers at the protein level in cell populations are also known in the art. For example, flow cytometry is used to determine the fraction of cells in a given cell population that express or do not express biological markers of interest.

In some cases, a 3D porcine tissue construct of the present invention further comprises isolated biological components. As used herein, an "isolated" biological component (such as a protein or organelle) has been substantially separated or purified away from other biological components in the cell of the organism in which the component naturally occurs, such as other chromosomal and extra-chromosomal DNA and RNA, proteins, and organelles. As used herein, the term "isolated protein" includes proteins purified by standard purification methods. The term also embraces proteins prepared by recombinant expression in a host cell, as well as chemically synthesized proteins, or fragments thereof.

In another aspect, provided herein is a use of a 3D scaffold-free porcine tissue described herein for drug screening, drug discovery, or drug response. In particular, provided herein are methods in which a 3D porcine tissue construct obtained as described herein is used to screen test compounds for known and unknown toxicities. For example, a 3D porcine liver tissue construct can be contacted to a test compound and assayed for any effect on any of the cell types contained therein (e.g., hepatocytes, LSECs, fibroblasts). In certain embodiments, screening methods comprise contacting one or more test compounds to a 3D porcine tissue construct obtained as described herein and detecting a positive or negative change in a biological property or activity such as, without limitation, gene expression, protein expression, cell viability, and cell proliferation. The manner in which a test compound has an effect on a particular biological activity of the constructs of the present invention will depend on the nature of the test compound, the composition of the tissue construct and the particular biological activity being assayed. However, methods of this disclosure will generally include the steps of (a) culturing a 3D porcine tissue construct obtained with a test compound, (b) assaying a selected biological activity of the synthetic 3D porcine tissue construct, and (c) comparing values determined in the assay to the values of the same assay performed using a synthetic 3D porcine tissue construct having the same composition as the construct contacted by the test compound but cultured in the absence of the test compound (or in the presence of a control). Detecting a positive or negative change in a biological property or activity of a cell of the synthetic 3D porcine tissue construct can comprise detecting at least one effect of a test compound on morphology or life span of a cell or tissue within the contacted tissue construct, whereby a test compound that reduces the life span of the cells or tissues or has a negative impact on the morphology of the cells or tissues is identified as toxic to that tissue. In some cases, detecting comprises performing a method such as RNA sequencing, gene expression profiling, transcriptome analysis, metabolome analysis, detecting reporter or sensor, protein expression profiling, Förster resonance energy transfer (FRET), metabolic profiling, and microdialysis. Test compounds can be screened for effects on gene expression in the contacted synthetic 3D porcine tissue construct, where differential gene expression as compared to an uncontacted synthetic tissue construct is detected.

In some cases, detecting and/or measuring a positive or negative change in a level of expression of at least one gene following exposure (e.g., contacting) of a synthetic 3D porcine tissue construct to a test compound comprises whole transcriptome analysis using, for example, RNA sequencing. In such cases, gene expression is calculated using, for example, data processing software programs such as Light Cycle, RSEM (RNA-seq by Expectation-Maximization), Excel, and Prism. See Stewart et al., *PLoS Comput. Biol.* 9:e1002936 (2013). Where appropriate, statistical comparisons can be made using ANOVA analyses, analysis of variance with Bonferroni correction, or two-tailed Student's t-test, where values are determined to be significant at P<0.05. Any appropriate method can be used to isolate RNA or protein from synthetic porcine liver tissue constructs. For example, total RNA can be isolated and reverse transcribed to obtain cDNA for sequencing.

In another aspect, the materials described above as well as other materials can be packaged together in any suitable combination as a kit useful for performing, or aiding in the performance of, a method provided herein. It is useful if the kit components in a given kit are designed and adapted for use together in the disclosed method. For example, disclosed herein are kits comprising a 3D scaffold-free synthetic porcine tissue produced by the disclosed methods. As another example, disclosed are kits comprising one or more of genetically engineered porcine cells, spheroids comprising genetically engineered porcine cells, and a microneedle mold for bioprinting of the porcine tissues provided herein. In some embodiments, kits also can contain one or more culture media, labels, and/or other reagents for the detection of biological markers, polypeptides, or nucleic acids of interest in the resulting 3D scaffold-free synthetic porcine tissue.

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Nucleic acids can be obtained using any suitable method, including those described by Maniatis et al., Molecular Cloning: A Laboratory Manual, Cold Spring Harbor, N.Y., pp. 280-281 (1982). In some aspects, nucleic acids are obtained as described in U.S. Patent Application Publication No. US2002/0190663. Nucleic acids obtained from biological samples typically are fragmented to produce suitable fragments for analysis.

Nucleic acids and/or other moieties of the invention may be isolated. As used herein, "isolated" means separate from at least some of the components with which it is usually associated whether it is derived from a naturally occurring source or made synthetically, in whole or in part. Nucleic acids and/or other moieties of the invention may be purified. As used herein, "purified" means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Each of the publications cited in this application is incorporated by reference in its entirety and for all purposes. While specific embodiments and examples of the disclosed subject matter have been discussed herein, these examples are illustrative and not restrictive. Many variations will become apparent to those skilled in the art upon review of this specification and the claims below. It is understood that certain adaptations of the invention described in this disclosure are a matter of routine optimization for those skilled in the art, and can be implemented without departing from the spirit of the invention, or the scope of the appended claims.

So that the methods and systems provided herein may more readily be understood, certain terms are defined:

In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. In the specification and in the claims, the terms "including" and "comprising" are open-ended terms and should be interpreted to mean "including, but not limited to . . . ." These terms encompass the more restrictive terms "consisting essentially of" and "consisting of."

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

Various exemplary embodiments of compositions and methods according to this invention are now described in the following non-limiting Examples. The Examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Figures 1A, 1B, 1C, 1D, 1E:
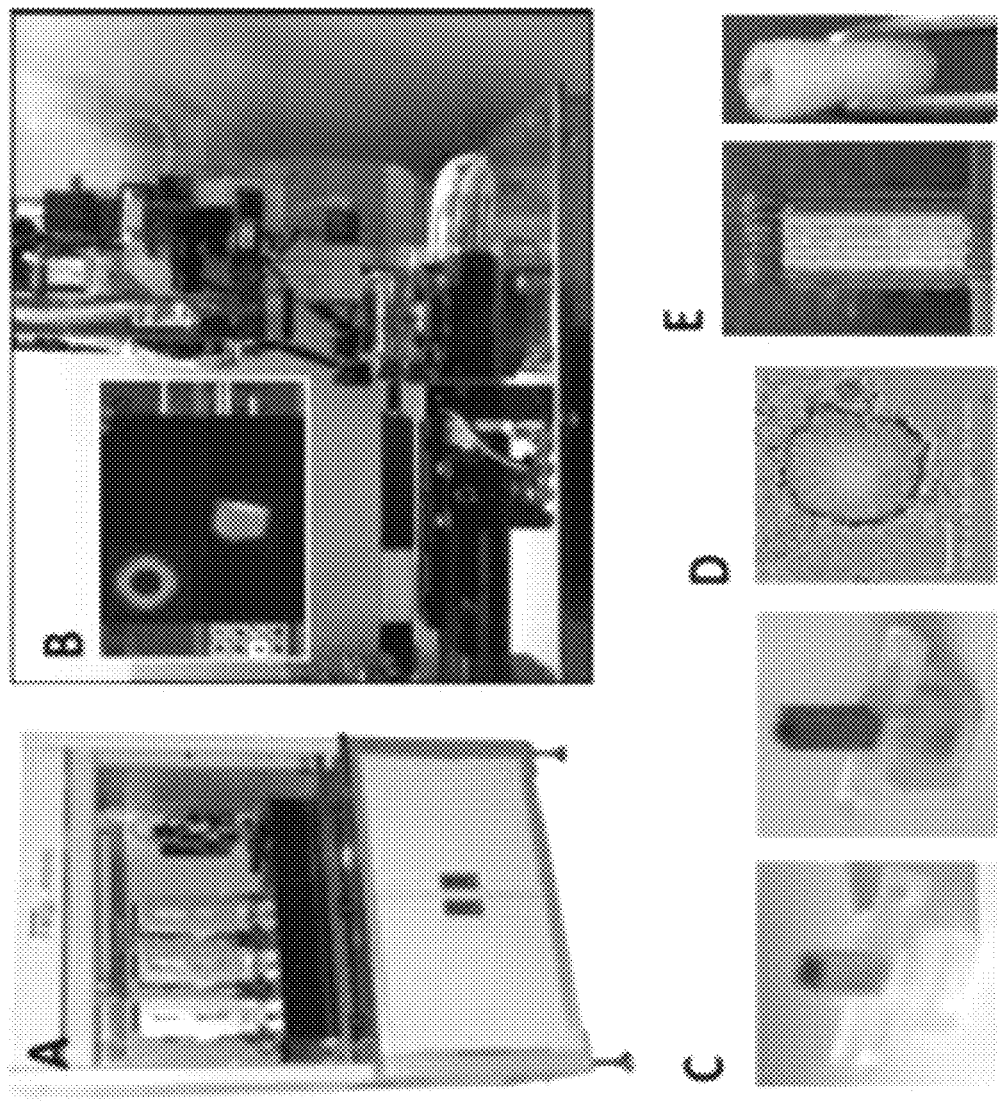
FIGS. 1A-1E demonstrate an exemplary bioprinting method and a Regenova bioprinter. A. The aseptic cabinet containing the Regenova robot (at 3D-bioprinting core at Indiana University-Purdue University of Indianapolis, Indiana University School of Medicine). B. Actual image of the instrument's robotic arm and the micro-needles holder (insert B: 3D design program, illustrating the construction of a layered cellular tube, as an example). C. Micro-needle arrays used for spheroids skewing (in two configurations). D. Before printing, the spheroids are checked for size and apoptosis at the core (green fluorescent substrate). E. A bioprinted tubular tissue construct (see cyfusebio.com on the World Wide Web).
Figures 2A, 2B, 2C, 2D, 2E, 2F, 2G, 2H, 2I, 2J:
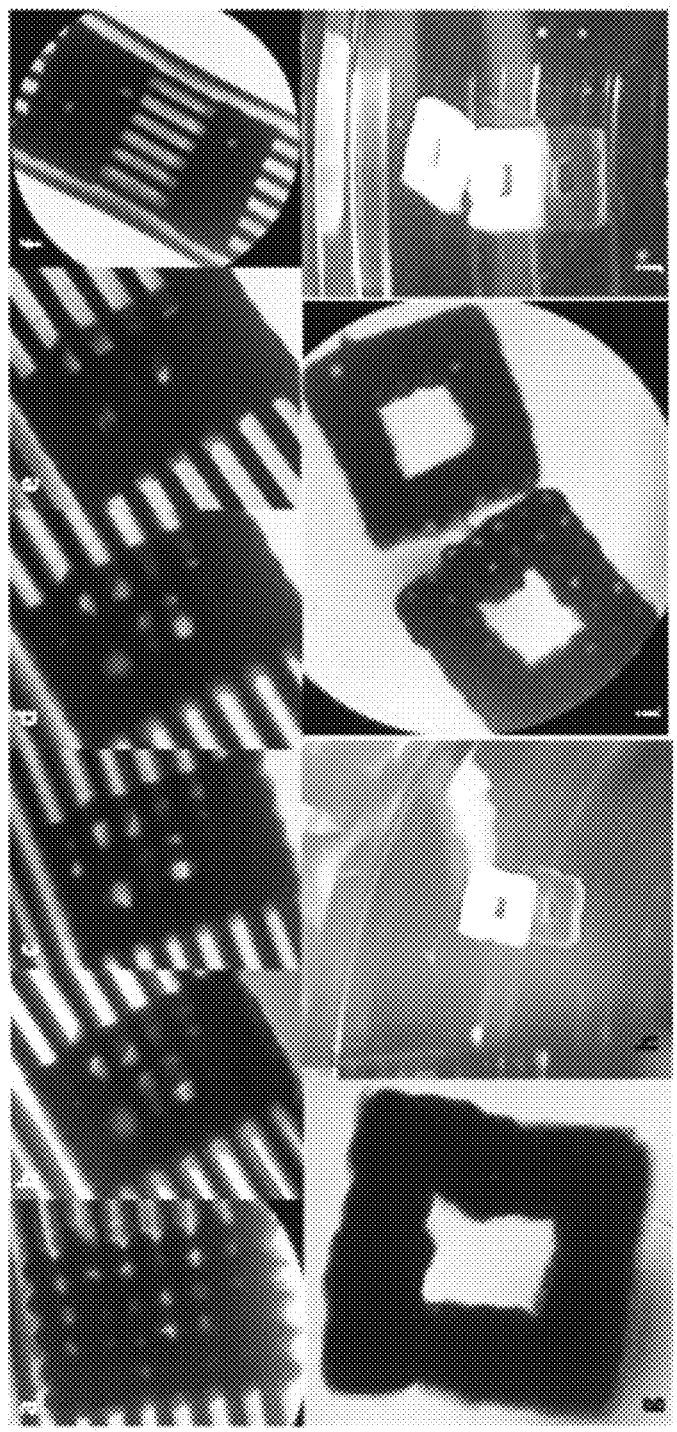
FIGS. 2A-2J demonstrate scaffold-free 3D-bioprinted fibroblasts and liver-derived cells (CD3 (A-E) show bioprinted combined wild-type porcine fibroblasts/liver derived cell containing spheroids and their fusion making 3D constructs on micro-needles from day 1 to day 5, respectively. (F) day 5 after 2 bioprinted constructs on microneedles. (G) microscope picture of scaffold-free 3D-bioprinted constructs moved out of microneedles. (H) The same construct as in image G as seen with naked-eye. (I) Both 3D constructs as shown in image F, removed from microneedles at the end of day 5. Micro-holes are visible in the constructs. (J) Naked-eye appearance of both 3D constructs as in image I.

Generating a Scaffold-Free 3D Bio-Assembled Genetically Engineered Pig Tissue/Liver Recently, a high-throughput instrument that is capable of assembling spheroids with precision has been developed: a Regenova bioprinter by Cyfuse Biomedical (Japan) (FIG. 1). In general, robotic platforms can assemble cell spheroids into predesigned contiguous structures with submillimeter-level three-dimensional (3D) precision, using an arrangement of microneedles as support. Using a Regenova bioprinter, we printed scaffold-free 3D constructs using wild-type (WT) and genetically-engineered pig cells onto Kenzan microneedles. Referring to FIGS. 2A-2J, we bioprinted spheroids comprising wild-type porcine fibroblasts and liver derived cells (LDCs). The bioprinted spheroids fused to form a three-dimensional construct of cellular aggregates upon the microneedles within the first five days following printing. On day 5, we removed the 3D constructs from the microneedles. Micro-holes were visible in the removed 3D constructs (FIG. 2I).

Figures 3A, 3B, 3C, 3D:
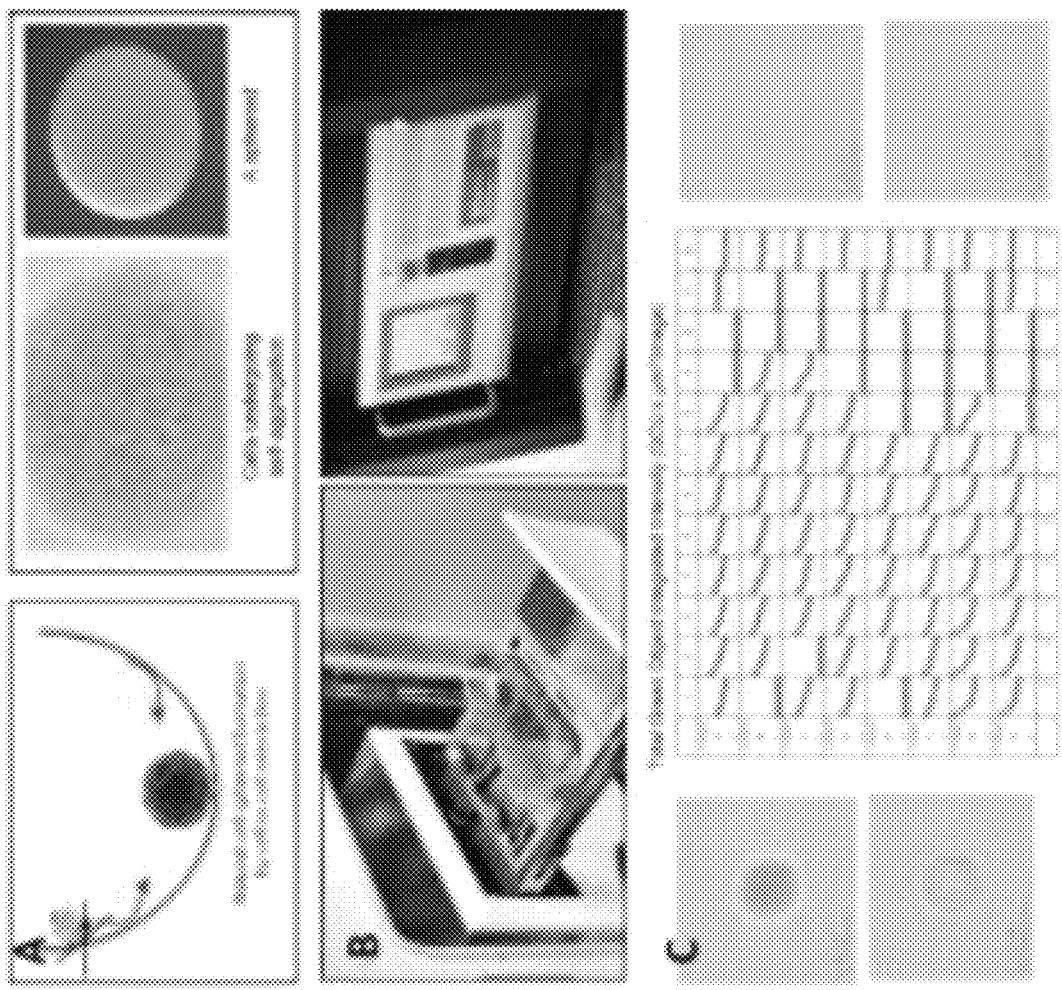
FIGS. 3A-3D demonstrate cell spheroid formation and analysis. A. Principle of cell aggregation in non-adhesive plates, and examples of spheroids. B. The IncuCyte ZOOM microscope, capable to analyze spheroid dynamics. C. Actual images of spheroids in fluorescence and phase contrast, and the recordings over a week, in a 96-well plate partially occupied with spheroids (right column, images from empty wells). D. 3D imaging of Green Fluorescence Protein (GFP) stained liver derived cells and their alignment in the spheroid formation with fibroblasts.

To determine the cell spheroid sizes and content that reproducibly yield uniform 3D bioprinted pig tissue constructs, we studied four variables: (i) diameter of spheroids, (ii) distance between spheroids from the center of each well, (iii) smoothness of spheroids, and (iv) roundness of spheroids. We prepared approximately 400-600 μm cell spheroids using wild-type and genetically engineered pig cells and assessed spheroid size 2, 3, 5, and 7 days after plating (see FIG. 3C). The efficiency of efficiency of spheroid formation was assessed by measuring the kinetics of percentage of area covered by cells using the IncuCyte® live-cell imaging and analysis system.

Figures 4A, 4B, 4C, 4D, 4E, 4F, 4G:
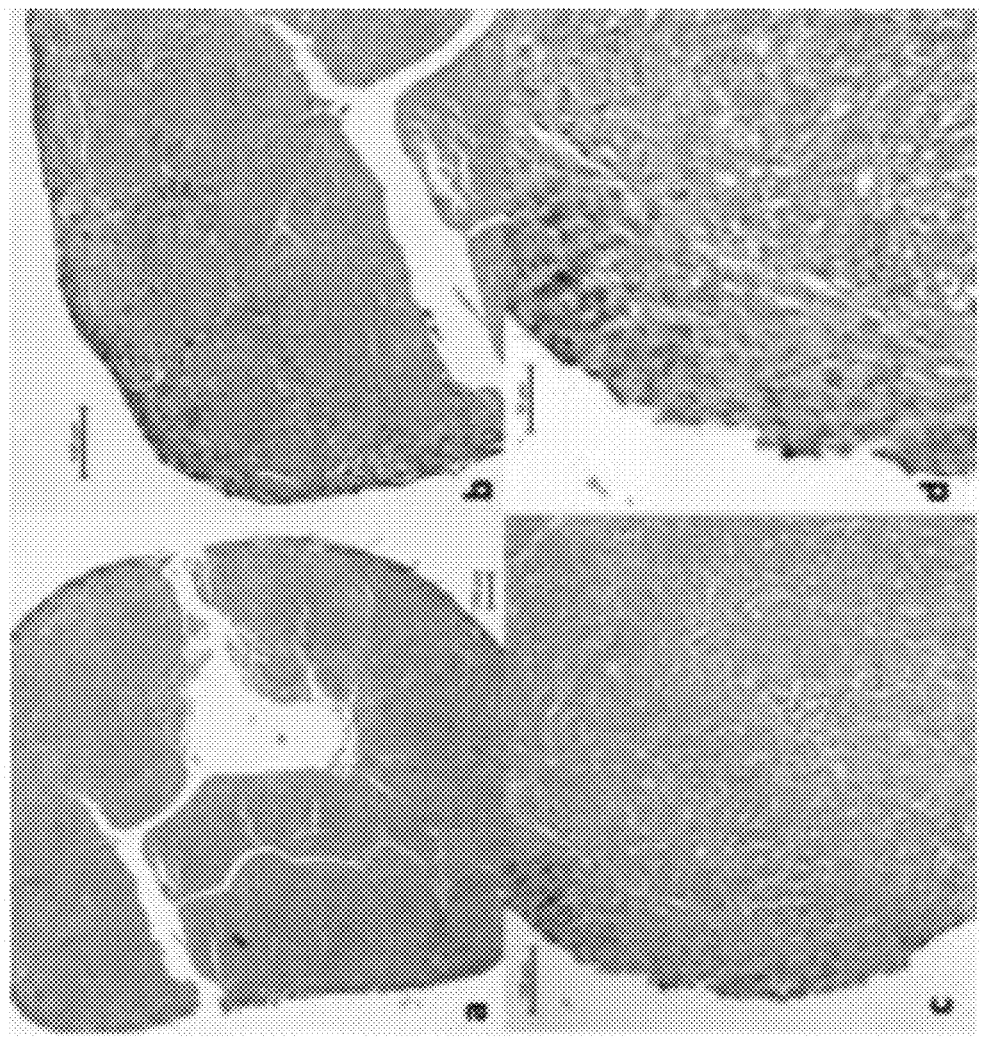
FIGS. 4A-4G present histopathology images of a scaffold-free 3D bioprinted construct. (a-b) 1-week after bioprinting. Capsules surrounding the 3D-construct and each spheroid with proliferating cells are visible with ×5 and ×10 magnification, respectively. Black bar indicates 100 μm (c-d) 2-weeks after bioprinting. Thicker capsules with proliferating and viable cells with ×10 and ×20 magnification, respectively. Black bar indicates 100 μm and 50 μm, respectively. (E-F). Histopathology of 3D-construct 3 weeks after bioprinting. ×10 and ×20 magnification show even thicker capsule than 2-week 3D-construct with proliferating cells and cells migrating to the center. 4G. Histology of 3 cell line (fibroblast/hepatocyte and liver endothelial cells) 3D-bioprinted liver construct 1 week after bioprinting. Although central necrosis is present, viable cells constitute ~80% of the 3D-construct. ×10 magnification.

Hematoxylin and eosin staining, immunohistochemistry, and confocal microscopy were also performed. Histopathology analysis revealed that capsules surrounded each 3D construct and each spheroid contained proliferating cells 1 week after bioprinting (FIGS. 4A-4B). Two weeks after bioprinting, thicker capsules comprising proliferating, viable cells were visible (FIGS. 4C-4D). Histopathology of a 3D-construct 3 weeks after bioprinting revealed a thicker capsule (relative to the 2-week 3D-construct) with proliferating cells and cells migrating to the center (FIGS. 4E-4F). From histology of a 3-cell line (fibroblasts, hepatocytes, and liver endothelial cells) 3D-bioprinted liver construct 1 week after bioprinting, we observed some central necrosis but also viable cells comprising about 80% of the synthetic construct (FIG. 4G).

Spheroid formation: Cells in low-binding microwells will bind to each other, thus forming a cell aggregate spheroid. Spheroid size is determined, in part, by cell number and culture time. It was observed that 10,000 to 50,000 cells of each type per spheroid generated 400-500 μm-diameter cell spheroids. ~500 μm is the appropriate size for Regenova Bioprinter assembly onto the Kenzan. This size also approximates the maximum nutrient diffusion distance (~200-250 μm from spheroid perimeter to center), meaning that cell respiration in the spheroid core can be maintained. Spheroids formed in 2 to 3 days, depending on cell type.

Printing: Wild type (WT)-skin fibroblasts were printed with 400-500 μm spheroids which formed after 2-3 days of plating the cells as described above. Although a hollow cylinder design was preferred for 3D bioprinting, WT-skin fibroblasts tended to fuse, and therefore, the central hole was closed rapidly without perfusion. Next, a combination of fibroblasts, hepatocytes, and liver-derived cells (CD31+) were used to form spheroids and printed to obtain a porcine liver model (FIG. 3). 3D-bioprinted liver constructs were matured for 1, 2, and 3 weeks in culture media. One 3D-bioprinted liver construct was continuously perfused with a set flow rate using the prototype bioreactor for one week. Hematoxylin/eosin (H/E) staining was performed on 3D-bioprinted liver constructs to detect viable cells (FIGS. 4A-4G).

Example 2

Scaffold-Free 3D-Bioprinting of a Liver Model

This example demonstrates production and printing of hepatocyte and hepatic stellate cell (HSC) spheroids to create a SF3DBP liver model. Briefly, freshly thawed primary pig hepatocytes and immortalized pig HSC were used to generate spheroids with (i) hepatocytes alone, (ii) HSC alone, or (iii) a combination of hepatocytes and HSC. Spheroids were formed using low adhesion plates, then characterized for distance from well center, diameter, roundness, and smoothness. A column of spheroids was printed using a Regenova 3D-bioprinter. Remaining loose spheroids were incubated over two weeks for functionality assays (albumin secretion, mRNA transcription, urea clearance).

Materials and Methods

Figure 11:
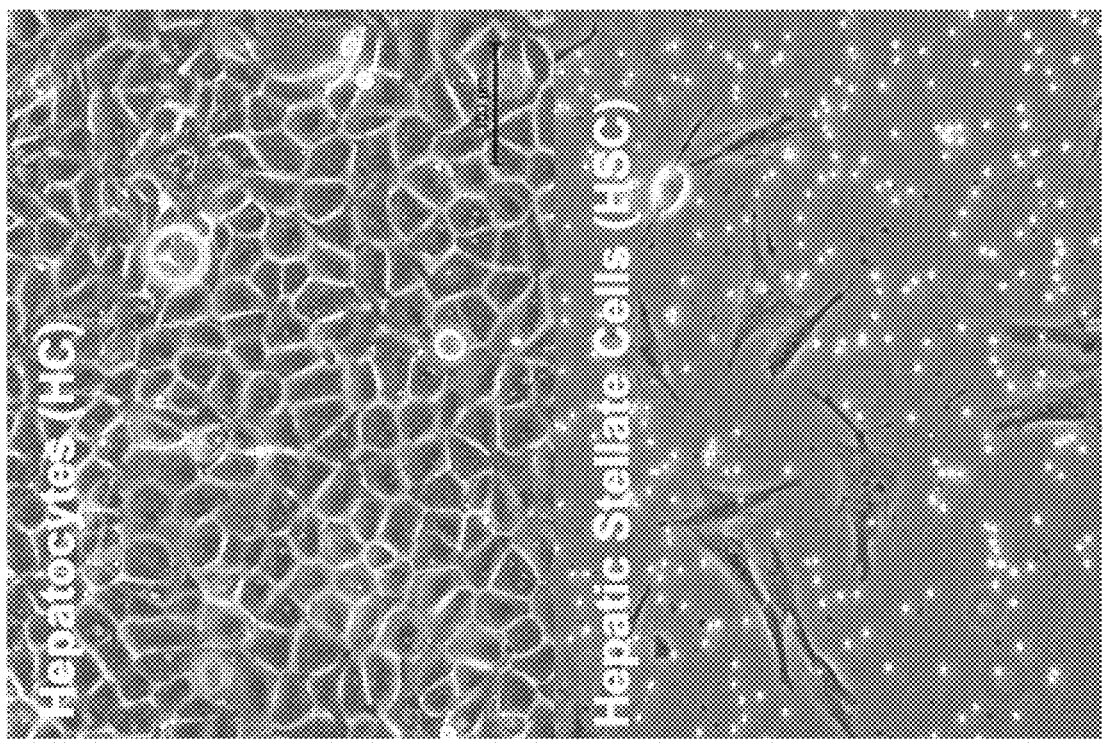
FIG. 11 demonstrates (top) isolated pig liver hepatocytes at 50× magnification and (bottom) pig liver hepatic stellate cells at 50× magnification.

Cell culture: Hepatocytes & HSCs were isolated from the liver of a 4-month old, healthy male pig (FIG. 11). HSC were immortalized using SV40T lentivirus. Immortalized HSCs were successfully cultured.

Spheroid formation: Previously isolated freshly thawed hepatocytes and immortalized HSCs (passage 6-9) were used to make spheroids. Cells were plated in Sbio low adhesion 96 well U-bottom plates (New Hampshire, USA).

Spheroid Characterization and 3D bioprinting: Spheroids were characterized for diameter, roundness, and smoothness using a Regenova Scaffold-Free 3D Bioprinter by Cyfsuse Biomedical (Tokyo, Japan). SF3DBP was conducted using a 9×9 Kenzan needle array in a 3×3×6 pattern.

Sample collection: Media samples were collected and at least 3 spheroids were sampled for mRNA per test group at days 3, 7, 11, and 14 days. Whole spheroids were also collected on days 7 and 15 to be fixed for immunohistochemical testing.

Albumin and Urea testing: Albumin (Pig Albumin Elisa kit, abcam) and urea concentrations were tested (QuantiChrom™ Urea Assay Kit, Fisher).

Real Time PCR analysis: Spheroid mRNA was extracted using a Qiagen RNeasy® kit. cDNA was synthesized using iScript™ cDNA synthesis kit (Biorad). Real Time PCR was performed on a Biorad CFX95Touch™.

Results & Discussion

Figures 12A, 12B:
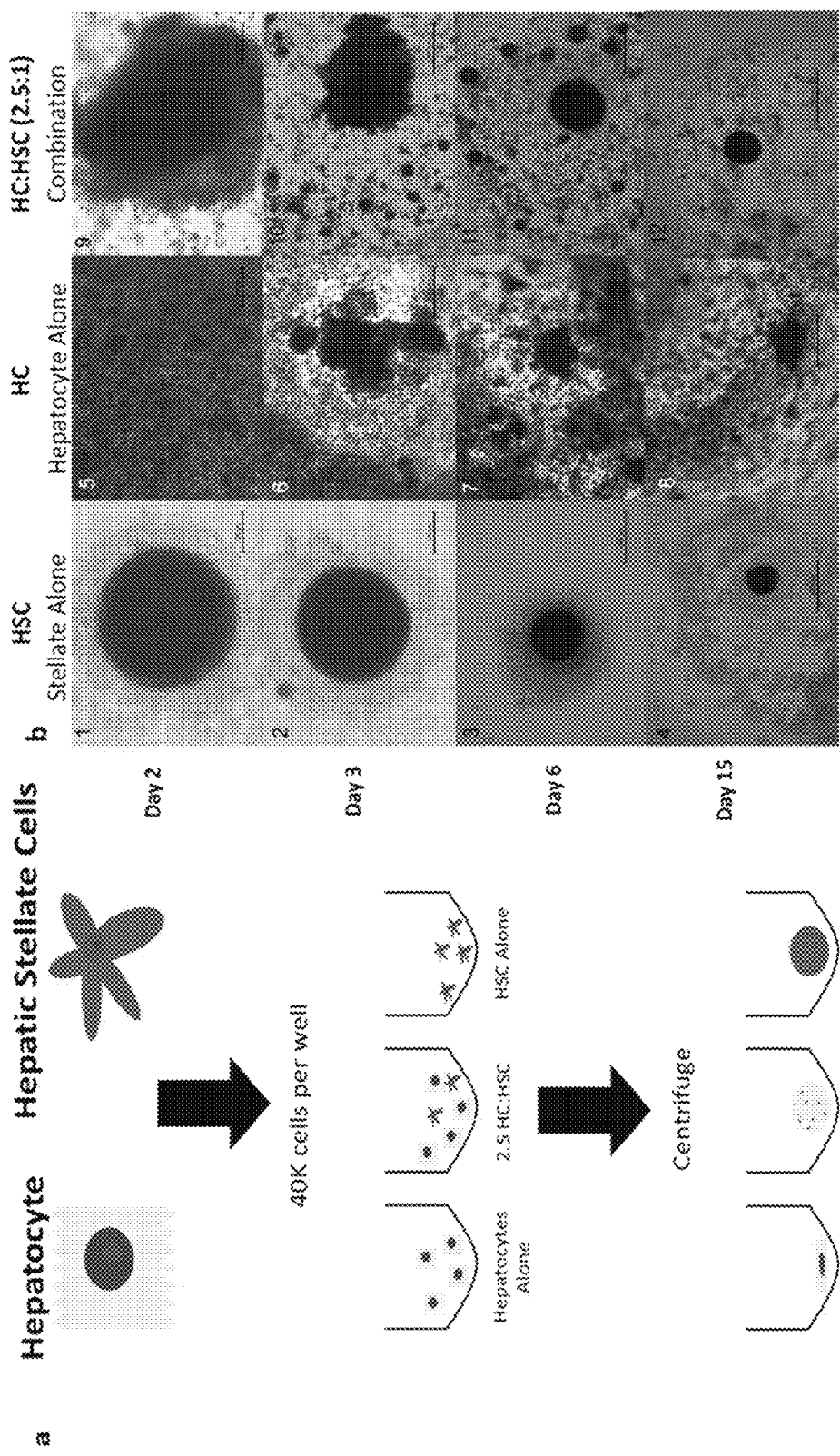
FIG. 12A illustrates an exemplary process of forming spheroids from free cells using low affinity U-bottom plates, centrifugation, and time. Spheroids were formed using (i) hepatocytes (HC) alone, (ii) hepatic stellate cells (HSC) alone, or (iii) combination of HC and HSC, cultured in low affinity U-bottom plates.
FIG. 12B demonstrates formation of spheroids over time using HC, HSC or their combination with 40,000 cells. Spheroids by HSC alone were uniformly round and smooth. HC alone spheroids failed to coalesce into a characterizable spheroids.
Figure 13:
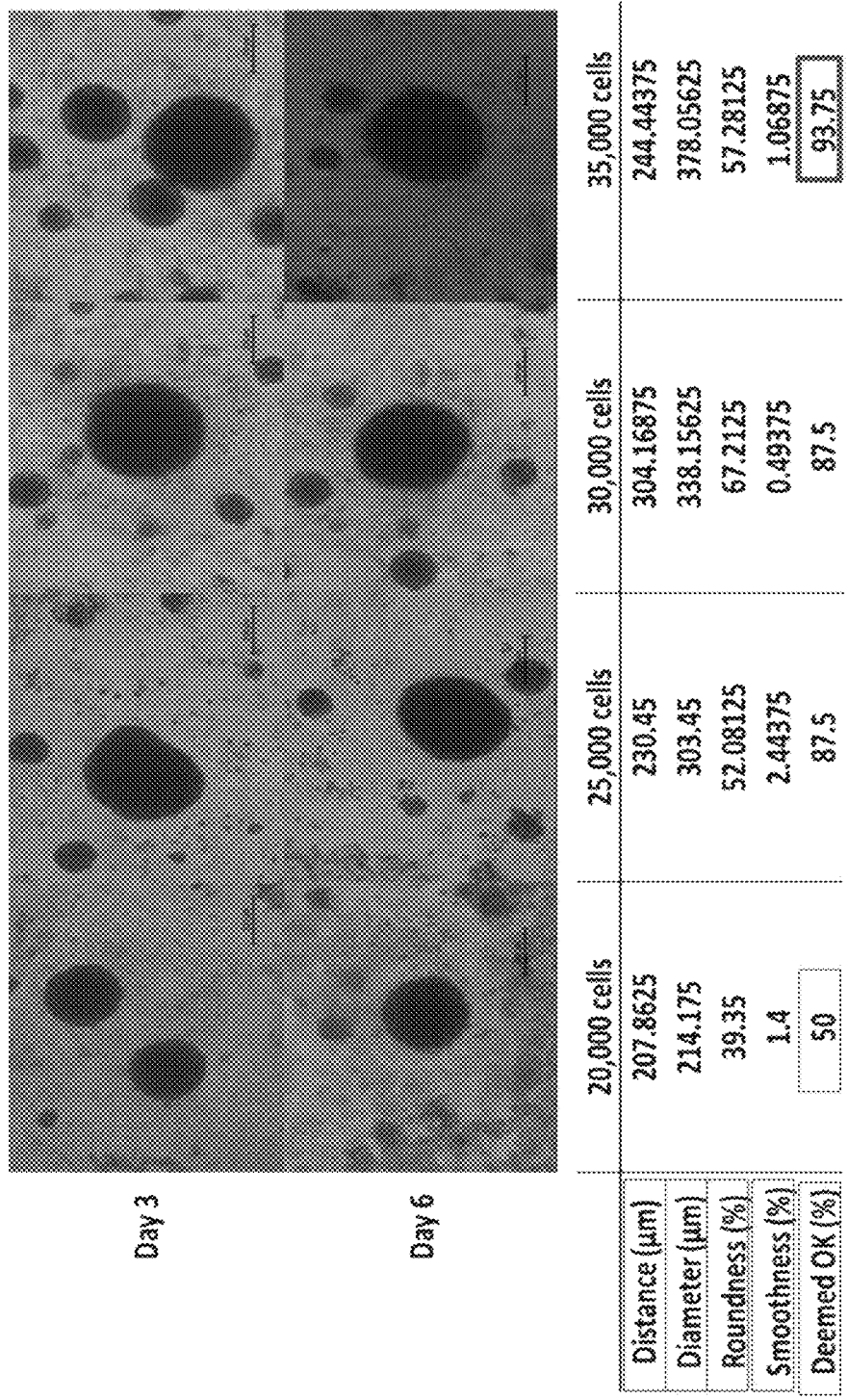
FIG. 13 presents images and data characterizing combination hepatocyte and HSC spheroids (2:1 ratio). Images demonstrate the formation of spheroids, with multiple smaller spheroids located on the periphery of each well. Characterization of spheroids occurred on Day 6. Smaller spheroids were less viable across all parameters.

As shown in FIGS. 12A-12B, a combination of hepatocytes & HSC (2.5:1 ratio) produced round and smooth spheroids that were of a printable size (450-550 μm) after 6 days. Size titration demonstrated that spheroids comprising <40,000 cells were too small to print. Fibroblast-only and HSC-only spheroids were uniformly round and smooth spheroids after 48 hours. Diameter decreased from 626.45±66.62 μm at Day 2 to 500.47±80.14 μm by day 6.

Hepatocyte-only cells failed to coalesce into a characterizable spheroid, though loose aggregates of cells were seen in several wells at Day 3 and Day 6. Combination wells formed loose spheroids in 42 of 96 wells by Day 2 and tighter "fried egg" spheroids by Day 3. Combination spheroids were round by day 6, and the periphery had aggregated to form several smaller spheroids. Diameter decreased from 880.57±100.15 μm at Day 2 to 506.09±118.90 μm by Day 6. By varying centrifuge and incubation times for spheroids, we produced a SF3DBP construct comprising hepatocytes and HSC (2:1) on day 4. Being able to print spheroids on day 4 as compared to day 6 increases the utility of future constructs for pharmacological, immunological, and hepatotoxicity testing. Preliminary print of hepatocytes and HSC (2.5:1 ratio) and HSC only 40,000 cell spheroids at 48 hrs.

Figures 14A, 14B:
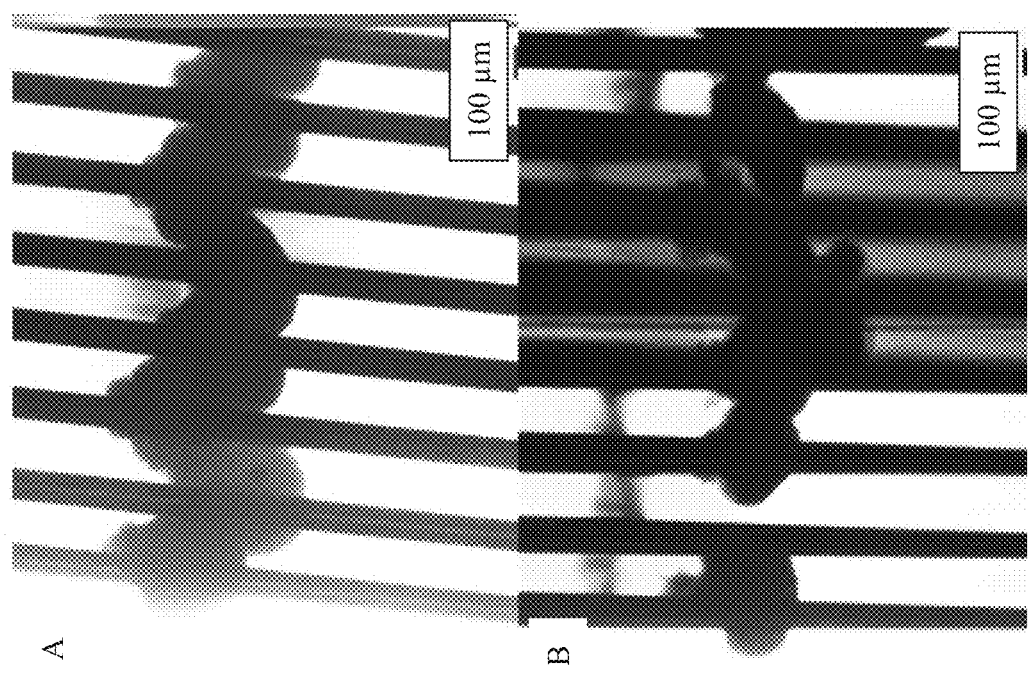
FIGS. 14A-14B. Preliminary print of hepatocytes and HSC (2.5:1 ratio) and HSC only 40,000 cell spheroids at 48 hrs. HSC spheroids printed in a stair step pattern, a result of their larger size (approximately 550 μm) (a). Combination spheroids were loose and not round or regular throughout the print, as evident by their smearing on the needle (b). Both constructs have a protrusion on top, a result of the nozzle sucking the spheroids partially inside of the printer arm. Printing was stopped, and spheroids were saved for functional analysis.

As shown in FIGS. 14A-14B, HSC spheroids printed in a stair step pattern, a result of their larger (550 μm) size (a). Combination spheroids were loose and not round or regular throughout the print, as evident by their smearing on the needle (b). Both constructs have a protrusion on top, a result of the nozzle sucking the spheroids partially inside of the printer arm. Printing was stopped, and spheroids were saved for functional analysis.

Figure 15:
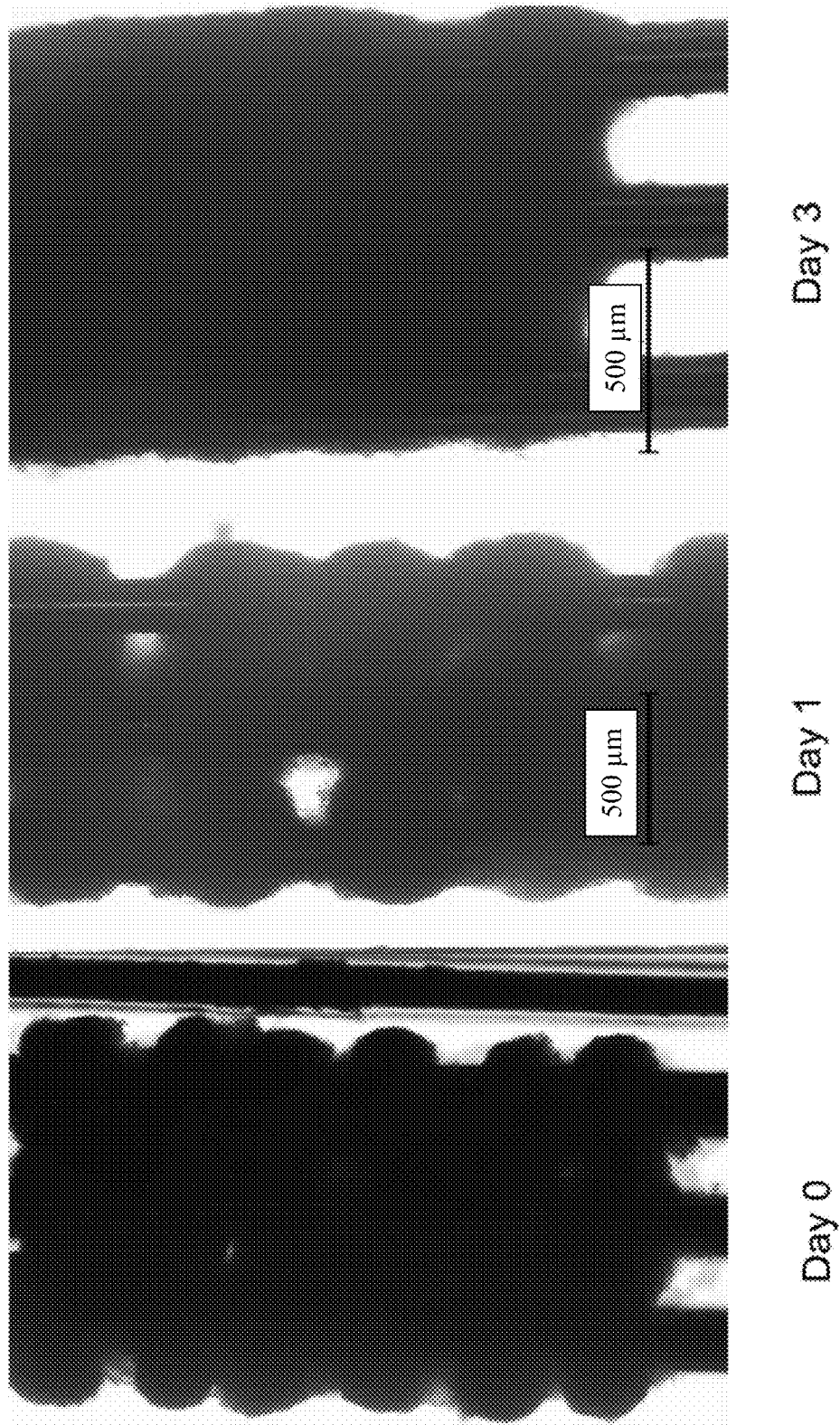
FIG. 15 illustrates hepatocyte and HSC (2:1 ratio) combination constructs following printing. Well-defined spheroids were visible on Day 0. Starting from day 1, spheroids fused to each other and made their own extracellular matrix. Gaps appeared in the constructs on Day 1, and the borders of the spheroid were less clear. By day 3, individual spheroids fused, thus creating one continuous tissue.

As shown in FIG. 15, a 3D-liver construct comprising combination spheroids was bioprinted on a temporary microneedle support from day 0 to day 3. By day 3, spheroids fused together forming their own extracellular matrix.

Figure 16A:
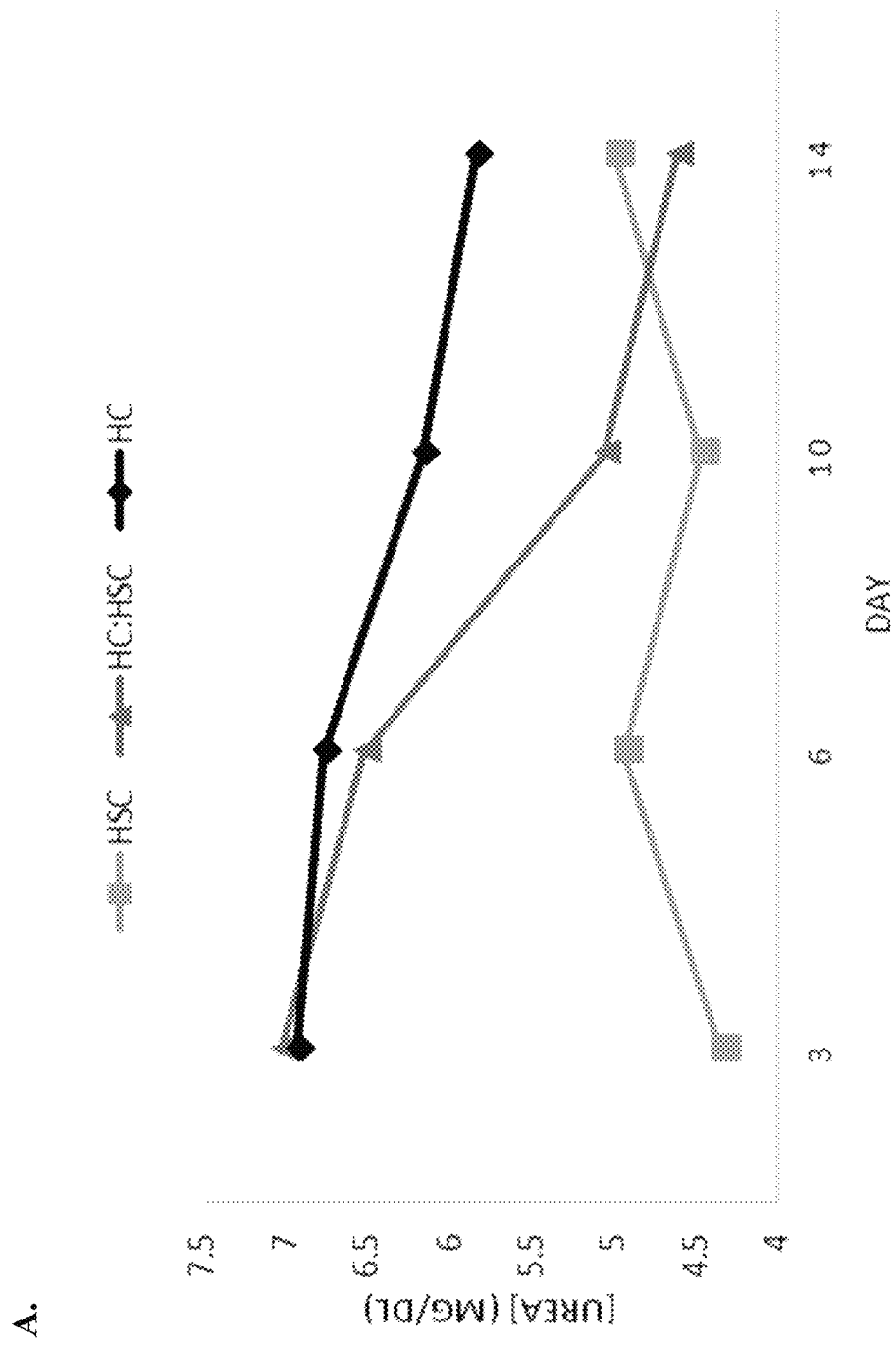
FIGS. 16A-16B demonstrate that hepatocytes remained metabolically active due to the support of HSC in spheroids.
Figure 16B:
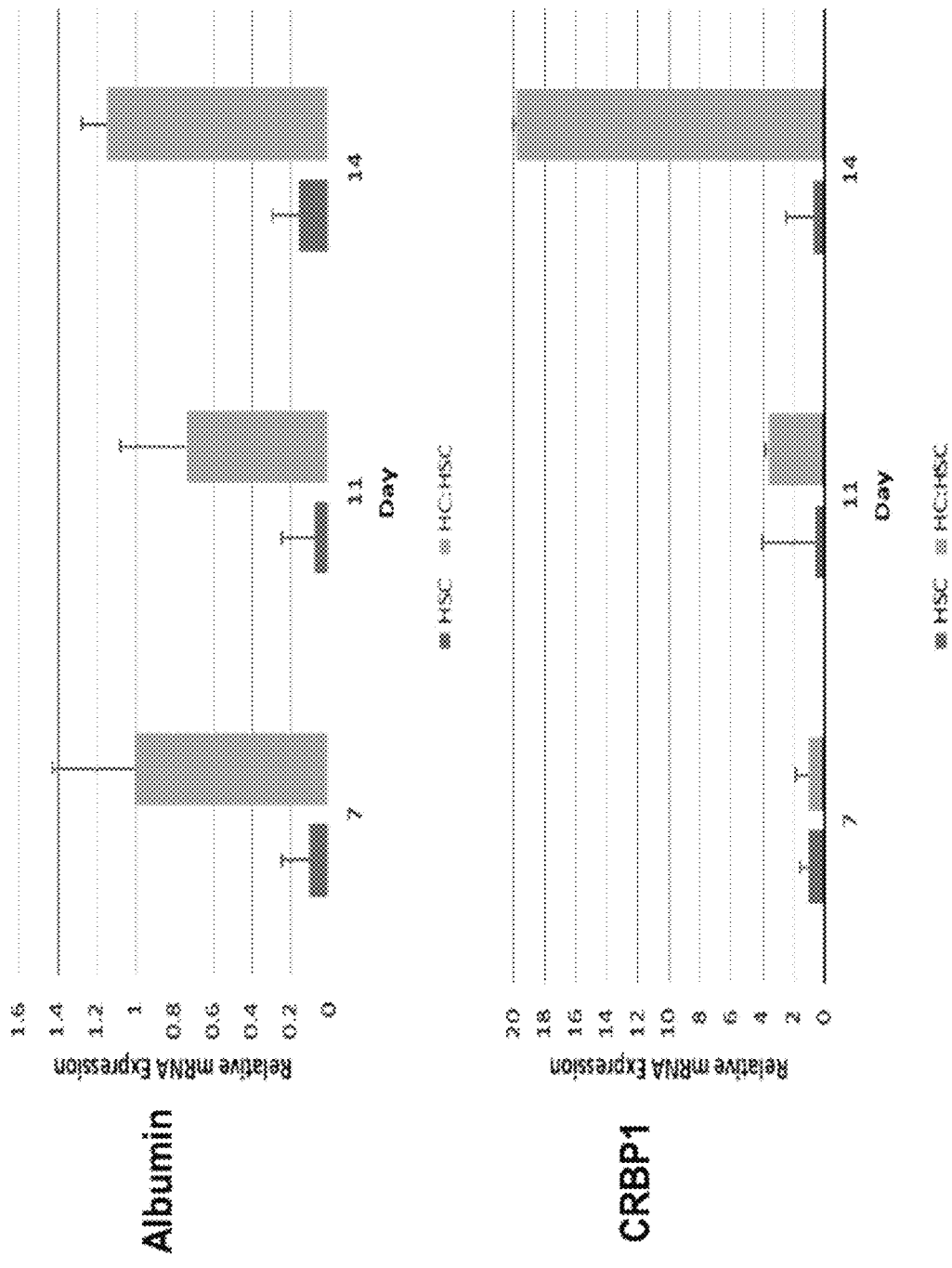

As shown in FIGS. 16A-16B, hepatocytes remain metabolically active due to the support of HSC in spheroids. Urea testing of 72-hour media samples showed a marked decrease in the urea concentration of the combination hepatocytes & HSC (2.5:1 ratio) spheroids over 2 weeks (FIG. 16A). Combination spheroids had the lowest value of urea clearance by day 14.

Real-time PCR demonstrated an increase in albumin mRNA expression in combination spheroids, showing a maintenance of functionality (FIG. 16B). CRBP-1 expression was also increased in combination spheroids. Hepatocyte samples had high Cq values, denoting limited transcription (FIG. 16B).

Spheroids formed by HSC alone proved too large to print at 48 hours. SF3DBP of spheroids (formed by hepatocyte: HSC in 2.5:1 ratio) would be viable by day 6. Optimization in centrifuging and incubation time allowed combination spheroids (2:1 ratio) to print earlier. Being able to print spheroids on day 4 as compared to day 6 increases the utility of future constructs for pharmacological, immunological, and hepatotoxicity testing. Maintenance of functionality of gene expression and albumin secretion emphasizes the utility of the 3D-bioprinted model over a period of 14 days. Further optimization of spheroids using different cell ratios including HSC, hepatocytes, liver sinusoidal endothelial cells, cholangiocytes, and fibroblasts will allow for production and printing of more physiologically accurate liver models.

Example 3

Scaffold-Free 3D-Bioprinting of Lung

Spheroids were formed using three types of porcine pulmonary cells: pulmonary vascular endothelial cells ($CD31^+$ve), pulmonary fibroblasts, and pulmonary pneumocytes Type II. Different ratios of pulmonary vascular endothelial cells, pulmonary fibroblasts, and pulmonary pneumocytes Type II were tested to form spheroids. The most suitable spheroids were formed using the ratio 1:1:1/2 of pulmonary vascular endothelial cells, pulmonary fibroblasts, and pulmonary pneumocytes Type II, respectively. Total cell numbers per spheroid was about 40,000 cells. Spheroids were bioprinted 2-3 days after they were matured in 96-well U bottom plate. A special hollow model computer design was chosen, as shown in FIG. 17 and spheroids were bioprinted on temporary microneedles (FIG. 17). Starting from day 1 post-bioprinting, spheroids starting to fuse making their own extracellular matrix (FIG. 18). By day 5 post-bioprinting, a solid, fused 3D lung construct was formed and was taken out of microneedle support having a free-standing scaffold-free 3D-bioprinted lung model (FIGS. 18-19).

FIGS. 20, 21, and 22 are histological images (stained with H&E) of free standing scaffold-free 3D-bioprinted lung model 2 days after removal of the support (7 days after the bioprint).

I claim:

1. A method for fabricating a synthetic three-dimensional (3D) porcine lung tissue construct, wherein the method comprises:
   providing a predetermined arrangement of microneedles;
   adding cell spheroids to the microneedles in a computer-controlled manner,
   wherein the cell spheroids are formed with porcine cells, comprising (1) CD31-positive pulmonary vascular endothelial cells, (2) pulmonary fibroblasts, and (3) pulmonary pneumocytes Type II at a ratio of 1:1:0.5, respectively, wherein the cell spheroids each comprise a total cell number of about 40,000 cells,
   wherein at least a portion of the porcine cells are genetically engineered; and
   culturing the spheroids on the microneedles for about 5 days whereby the spheroids fuse to form a synthetic 3D porcine lung tissue construct comprising genetically engineered porcine cells.

2. The method of claim 1, further comprising removing the synthetic 3D porcine lung tissue construct from the microneedles to obtain a scaffold-free synthetic 3D porcine lung tissue construct comprising genetically engineered porcine cells, wherein the 3D porcine lung tissue construct comprises an extracellular matrix prior to removal from the microneedle mold.

3. The method of claim 1, wherein the cell spheroids are bioprinted 2-3 days after maturation.

* * * * *

UNITED STATES PATENT AND TRADEMARK OFFICE
CERTIFICATE OF CORRECTION

PATENT NO. : 11,479,752 B2
APPLICATION NO. : 16/162921
DATED : October 25, 2022
INVENTOR(S) : Burcin Ekser It is certified that error appears in the above-identified patent and that said Letters Patent is hereby corrected as shown below:

In the Specification

Column 3, Line 37, "(CD3" should be --(CD31$^+$)--.

Signed and Sealed this
Twenty-second Day of August, 2023

Katherine Kelly Vidal
*Director of the United States Patent and Trademark Office*